(12) United States Patent
Espensen et al.

(10) Patent No.: US 9,428,498 B2
(45) Date of Patent: Aug. 30, 2016

(54) SUBSTITUTED IMIDAZO[4,5-C]PYRIDINE COMPOUNDS AND COMPOSITIONS THEREOF

(71) Applicant: Proximagen Limited, London (GB)

(72) Inventors: Max Espensen, London (GB); Lee Patient, London (GB); David Evans, London (GB); Edward Savory, London (GB); Iain Simpson, London (GB)

(73) Assignee: Proximagen Limited, London (GB)

( * ) Notice: Subject to any disclaimer, the term of this patent is extended or adjusted under 35 U.S.C. 154(b) by 190 days.

(21) Appl. No.: 14/208,056

(22) Filed: Mar. 13, 2014

(65) Prior Publication Data

US 2014/0275040 A1     Sep. 18, 2014

(30) Foreign Application Priority Data

Mar. 13, 2013  (GB) .................................. 1304526.5

(51) Int. Cl.
| | | |
|---|---|---|
| *C07D 471/02* | (2006.01) | |
| *C07D 515/02* | (2006.01) | |
| *A61K 31/44* | (2006.01) | |
| *C07D 471/04* | (2006.01) | |

(52) U.S. Cl.
CPC .................................. *C07D 471/04* (2013.01)

(58) Field of Classification Search
CPC .............................. C07D 471/04; A61K 31/40
USPC ................... 546/112, 118, 373; 514/926, 927
See application file for complete search history.

(56) References Cited

U.S. PATENT DOCUMENTS

| 7,405,300 B2 * | 7/2008 | Jiang et al. .................... 544/373 |
|---|---|---|
| 2005/0054631 A1 | 3/2005 | Jiang et al. |

FOREIGN PATENT DOCUMENTS

| WO | 02/38153 A1 | 5/2002 |
|---|---|---|
| WO | 03/006003 A1 | 1/2003 |
| WO | 2005/014530 A2 | 2/2005 |
| WO | 2007/120528 A2 | 10/2007 |
| WO | 2010/031789 A1 | 3/2010 |
| WO | 2010031791 A1 | 3/2010 |
| WO | 2010064020 A1 | 6/2010 |
| WO | 2010/117935 A1 | 10/2010 |
| WO | 2011113798 A2 | 9/2011 |
| WO | 2013037411 A1 | 3/2013 |
| WO | 2013038189 A1 | 3/2013 |
| WO | 2013/078254 A1 | 5/2013 |
| WO | 2014/140592 A1 | 9/2014 |

OTHER PUBLICATIONS

Search Report from Great Britain Patent Application 1304526.5 filed Mar. 13, 2013.
International Search Report, mailed on May 8, 2014, for PCT/GB2014/05076 filed on Mar. 13, 2014.
Database Registry [online], Chemical Abstracts Service, Columbus, Ohio, US; Jan. 19, 2011, XP002723294, database accession No. 1259952-23-2 abstract.
Melkonyan, Ferdinand S., et al. "One-pot synthesis of substituted indoles via titanium(iv) alkoxide mediated imine formation—copper-catalyzed N-arylation," RSC Advances, vol. 3, No. 22, Mar. 21, 2013, p. 8388, XP055113497.
Wilson, Robert J., et al. "Copper- and Palladium-Catalyzed Amidation Reactions for the Synthesis of Substituted Imidazo[4,5-c]pyridines," The Journal of Organic Chemistry, vol. 79, No. 5, Feb. 6, 2014, pp. 2203-2212, XP055113503.
Dunkel, Petra et al. "Semicarbazide-sensitive amine oxidase/vascular adhesion protein-1: a patent survey," Expert Opin. Ther. Patents, 21(9): 1453-1471 (2011).

* cited by examiner

*Primary Examiner* — Andrew D Kosar
*Assistant Examiner* — Raymond Covington
(74) *Attorney, Agent, or Firm* — Sean B. Mahoney; Upsher-Smith Laboratories, Inc.

(57) ABSTRACT

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumor growth.

16 Claims, No Drawings

SUBSTITUTED IMIDAZO[4,5-C]PYRIDINE COMPOUNDS AND COMPOSITIONS THEREOF

This application claims priority under 35 U.S.C. 119 to Great Britain Patent Application No. 1304526.5, filed Mar. 13, 2013, which is incorporated herein by reference in its entirety.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

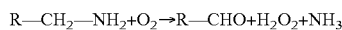

R—CH$_2$—NH$_2$+O$_2$→R—CHO+H$_2$O$_2$+NH$_3$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557]. It has recently been shown that circulating human and rodent SSAO originates from the tissue-bound form [Gökürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Cur. Med. Chem.* 2004, 11(10), 1285-1298; O'Sullivan et al., *Neurotoxicology* 2004, 25(1-2), 303-315; del Mar Hernandez at al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang at al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda at al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. VAP-1 has also been implicated in the progression and maintenance of fibrotic diseases including those of the liver and lung. Weston and Adams (J Neural Transm. 2011, 118(7), 1055-64) have summarised the experimental data implicating VAP-1 in liver fibrosis, and Weston at al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88; Irjala H, Salmi M, Alanen K, Grénman R, Jalkanen S (2001), Immunol. 166, 8937-6943; Forster-Horvath C, Dome B, Paku S, et al. (2004), Melanoma Res. 14, 135-40.). One report (Marttila-Ichihara F, Castermans K, Auvinen K, Oude Egbrink M G, Jalkanen S, Griffoen A W, Salmi M. (2010), J Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in PCT/EP2009/062011 and PCT/EP2009/062018. Additional SSAO inhibitors are disclosed in PCT/GB2012/052265.

The invention described here relates to a new class of SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

DETAILED DESCRIPTION OF THE INVENTION

It has surprisingly been found that the compounds of formula (I) below are inhibitors of SSAO. They are therefore useful for the treatment or prevention of diseases in which inhibition of SSAO activity is beneficial, such as inflammation, inflammatory diseases, immune or autoimmune disorders, and inhibition of tumour growth.

According to the invention there is provided a compound of formula (I) or a pharmaceutically acceptable salt, or N-oxide thereof:

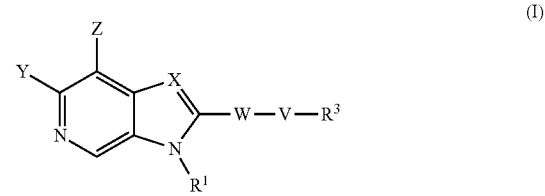

Wherein:

Y is selected from hydrogen, hydroxyl, —$NH_2$, —NH—$C_{1-4}$-alkyl, —NH-halo-$C_{1-4}$-alkyl, or —$C_{1-4}$-alkoxy;

Z is selected from hydrogen, halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, or —$NH$halo-$C_{1-4}$-alkyl;

$R^1$ is a phenyl ring, or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, and —$NR^6S(O)_2R^5$; wherein $R^{4A}$, $R^{4B}R^5$ and $R^6$ are each independently selected from hydrogen, $C_{1-4}$-alkyl or halo-$C_{1-4}$-alkyl, or $R^{4A}$ and $R^{4B}$ together with the nitrogen to which they are attached form a 3-7 membered cyclic amino group, optionally substituted by one or more substituents selected from: halogen, hydroxyl, cyano, C-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, —$NH$halo-$C_{1-4}$-alkyl;

X is selected from —N= or —$C(R^2)$=;

$R^2$ is selected from hydrogen, halogen, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$;

W is a phenyl ring or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^{7A}R^{7B}$, —$NR^6C(O)OR^5$, —$NR^6C(O)R^5$, —$NR^6C(O)NR^{7A}R^{7B}$, —$C(O)$ NR$^{7A}$R$^{7B}$, —C(O)R$^5$, —C(O)OR$^5$, —SO$_2$R$^5$, —SO$_2$NR$^{7A}$R$^{7B}$ and —NR$^6$S(O)$_2$R$^5$;

R$^{7A}$ and R$^{7B}$ are independently hydrogen, C$_{1-4}$-alkyl or halo-C$_{1-4}$-alkyl.

V is selected from a bond, —O—, —N(R$^6$)—, —(C=O)—, —CONR$^6$—, —NR$^6$C(O)—, or —C$_{1-4}$-alkylene-, wherein the C$_{1-4}$-alkylene group is optionally substituted by halogen, and wherein any one of the carbon atoms of the C$_{1-4}$-alkylene group may be replaced by —O— or —N(R$^6$)—;

R$^3$ is hydrogen or a 3-7 membered heterocyclic ring or 3-7 membered cycloalkyl ring, or a 5 or 6-membered heteroaryl ring, any one of the rings being optionally substituted with one or more substituents selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)R$^5$.

In addition to the surprising activity of the compounds of formula (I) at the SSAO receptor, it has been surprisingly fund that the claimed compounds have surprisingly low activity at the hERG ion channel. The person skilled in the art, for example a medicinal chemist, understands that low hERG activity is an important property for a pharmaceutical drug compound. Without wishing to be bound by theory, it is believed that the —WVR$^3$ group as defined in claim 1 is especially advantageous in relation to reduced hERG activity.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

Since compounds of the invention have a nitrogen atom in an aromatic ring they may form N-oxides, and the invention includes compounds of the invention in their N-oxide form.

DEFINITIONS

The following definitions shall apply throughout the specification and the appended claims, unless otherwise stated or indicated.

The term "C$_{1-4}$-alkyl" denotes a straight or branched alkyl group having from 1 to 4 carbon atoms. For parts of the range C$_{1-4}$-alkyl all subgroups thereof are contemplated such as C$_{1-3}$-alkyl, C$_{1-2}$-alkyl, C$_{2-4}$-alkyl, C$_{2-3}$-alkyl and C$_{3-4}$-alkyl. Examples of said C$_{1-4}$-alkyl include methyl, ethyl, n-propyl, isopropyl, n-butyl, isobutyl, sec-butyl and tert-butyl.

Unless otherwise specified, the term "C$_{3-7}$-cycloalkyl" refers to a monocyclic saturated or partially unsaturated hydrocarbon ring system having from 3 to 7 carbon atoms.

Examples of said C$_{3-7}$-cycloalkyl include cyclopropyl, cyclobutyl, cyclopentyl, cyclohexyl, cyclohexenyl, cycloheptyl, and cycloheptenyl. For parts of the range "C$_{3-7}$-cycloalkyl" all subgroups thereof are contemplated such as C$_{3-7}$-cycloalkyl, C$_{3-6}$-cycloalkyl, C$_{3-5}$-cycloalkyl, C$_{3-4}$-cycloalkyl, C$_{4-7}$-cycloalkyl, C$_{4-6}$-cycloalkyl, C$_{4-5}$-cycloalkyl, C$_{5-7}$-cycloalkyl, C$_{5-6}$-cycloalkyl, and C$_{6-7}$-cycloalkyl.

The term "C$_{1-4}$-alkoxy" refers to a straight or branched C$_{1-4}$-alkyl group which is attached to the remainder of the molecule through an oxygen atom. For parts of the range C$_{1-4}$-alkoxy, all subgroups thereof are contemplated such as C$_{1-3}$-alkoxy, C$_{1-2}$-alkoxy, C$_{2-4}$-alkoxy, C$_{2-3}$-alkoxy and C$_{3-4}$-alkoxy. Examples of said C$_{1-4}$-alkoxy include methoxy, ethoxy, n-propoxy, isopropoxy, n-butoxy, isobutoxy, sec-butoxy and tert-butoxy.

The term "haloC$_{1-4}$-alkoxy" refers to a straight or branched C$_{1-4}$-alkyl group which is attached to the remainder of the molecule through an oxygen atom and has one or more hydrogen atoms thereof replaced with halogen such as fluoro or chloro. For parts of the range C$_{1-4}$-alkoxy, all subgroups thereof are contemplated. Examples of said C$_{1-4}$-alkoxy include trifluoromethoxy.

The term "hydroxy-C$_{1-4}$-alkyl" denotes a straight or branched C$_{1-4}$-alkyl group that has one or more hydrogen atoms thereof replaced with OH. Examples of said hydroxy-C$_{1-4}$-alkyl include hydroxymethyl, 2-hydroxyethyl and 2,3-dihydroxypropyl.

The term "halo-C$_{1-4}$-alkyl" denotes a straight or branched C$_{1-4}$-alkyl group that has one or more hydrogen atoms thereof replaced with halogen. Examples of said halo-C$_{1-4}$-alkyl include fluoromethyl, trifluoromethyl, trichloromethyl and 2-fluoroethyl.

The term "cyano-C$_{1-4}$-alkyl" denotes a straight or branched C$_{1-4}$-alkyl group that has one or more hydrogen atoms thereof replaced with cyano. Examples of said cyano-C$_{1-4}$-alkyl include cyanomethyl, 2-cyanoethyl and 3-cyanopropyl.

The term "amino-C$_{1-4}$-alkyl" denotes a straight or branched C$_{1-4}$-alkyl group substituted with an amino group. Examples of said amino-C$_{1-4}$-alkyl group include aminomethyl and 2-aminoethyl.

The term "C$_{1-4}$-alkylamino-C$_{1-4}$-alkyl" denotes an amino-C$_{1-4}$-alkyl group as defined above, wherein the amino group is substituted with a straight or branched C$_{1-4}$-alkyl group. Examples of said C$_{1-4}$-alkylamino-C$_{1-4}$-alkyl include methylaminoethyl and ethylaminopropyl.

The term "di(C$_{1-4}$-alkyl)amino-C$_{1-4}$-alkyl" denotes an amino-C$_{1-4}$-alkyl group as defined above, wherein the amino group is disubstituted with straight or branched C$_{1-4}$-alkyl groups, which can be the same or different. Examples of said di(C$_{1-4}$-alkyl)amino-C$_{1-4}$-alkyl include N,N-dimethylaminomethyl, N-ethyl-N-methylaminoethyl and N,N-diethylaminomethyl.

The terms "heteroaryl" and "heteroaromatic ring" denote a monocyclic heteroaromatic ring comprising 5 to 6 ring atoms in which one or more of the ring atoms are other than carbon, such as nitrogen, sulphur or oxygen. Examples of heteroaryl groups include furyl, pyrroyl, thienyl, oxazolyl, isoxazolyl, imidazolyl, thiazolyl, isothiazolyl, pyridinyl, pyrimidinyl, tetrazolyl, pyrazolyl, pyridazinyl, pyrazinyl and thiadiazolyl.

The terms "heterocyclyl" and "heterocyclic ring" denote a non-aromatic, fully saturated or partially unsaturated, preferably fully saturated, monocyclic ring system having from 3 to 7 ring atoms, especially 5 or 6 ring atoms, in which one or more of the ring atoms are other than carbon, such as nitrogen, sulphur or oxygen. Examples of heterocyclic groups include piperidinyl, morpholinyl, homomorpholinyl, azepanyl, piperazinyl, oxo-piperazinyl, diazepinyl, tetrahydropyridinyl, tetrahydropyranyl, pyrrolidinyl, tetrahydrofuranyl, and dihydropyrrolyl, groups.

The term "heterocyclic-$C_{1-4}$-alkyl" refers to a heterocyclic ring that is directly linked to a straight or branched $C_{1-4}$-alkyl group via a carbon or nitrogen atom of said ring. Examples of said heterocyclic-$C_{1-4}$-alkyl include piperidin-4-ylmethyl piperidin-1-ylmethyl, morpholin-4-yl-methyl and piperazin-4-ylmethyl. The $C_{1-4}$-alkyl part, which includes methylene, ethylene, propylene or butylene, is optionally substituted by one or more substituents selected from halogen, amino, methoxy, or hydroxyl.

The term "$C_{1-4}$-alkylene" denotes a straight or branched divalent saturated hydrocarbon chain having from 1 to 4 carbon atoms. The $C_{1-4}$-alkylene chain may be attached to the rest of the molecule and to the radical group through one carbon within the chain or through any two carbons within the chain. Examples of $C_{1-4}$-alkylene radicals include methylene [—$CH_2$—], 1,2-ethylene [—$CH_2$—$CH_2$—], 1,1-ethylene [—$CH(CH_3)$—], 1,2-propylene [—$CH_2$—CH($CH_3$)—] and 1,3-propylene [—$CH_2$—$CH_2$—$CH_2$—]. When referring to a "$C_{1-4}$-alkylene" radical, all subgroups thereof are contemplated, such as $C_{1-2}$-alkylene, $C_{2-3}$-alkylene, or $C_{3-4}$-alkylene.

"Halogen" refers to fluorine, chlorine, bromine or iodine, preferably fluorine and chlorine, most preferably fluorine.

"Hydroxy" refers to the —OH radical.

"Cyano" refers to the —CN radical.

"Oxo" refers to the carbonyl group =O.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, $2^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic adds such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino adds, such as, e.g. arginine and lysine. The term addition salt as used herein also comprises solvates which the compounds and salts thereof are able to form, such as, for example, hydrates, alcoholates and the like.

The Group Y

In an embodiment Y is from hydrogen, hydroxyl, —$NH_2$, —NH—$C_{1-4}$-alkyl such as —NH-Methyl, —NH-ethyl, or —NH-isopropyl, —NH-halo-$C_{1-4}$-alkyl such as —NHtrifluoromethyl, or —$C_{1-4}$-alkoxy such as methoxy. In an embodiment Y is hydrogen.

The Group Z

In an embodiment Z is hydrogen, halogen such as fluoro or chloro, hydroxyl, cyano, $C_{1-4}$-alkyl such as methyl or isopropyl, halo-$C_{1-4}$-alkyl such as trifluoromethyl, $C_{1-4}$-alkoxy such as methoxy, halo-$C_{1-4}$-alkoxy such as trifluoromethoxy, —$CONH_2$, —$SO_2NH_2$, —$NH_2$, —$NHC_{1-4}$-alkyl such as —NH-Methyl, —NH-ethyl, or —NH-isopropyl, or —NHhalo-$C_{1-4}$-alkyl. In an embodiment Z is hydrogen.

The Group $R^1$

In an $R^1$ embodiment is a phenyl ring, or a 5 or 6-membered heteroaryl ring either ring being optionally substituted with one or more substituents selected from halogen such as fluoro or chloro, cyano, $C_{1-4}$-alkyl such as methyl or isopropyl, halo-$C_{1-4}$-alkyl such as trifluoromethyl, cyano-$C_{1-4}$-alkyl such as methylcyano, —$OR^5$ such as methoxy or trifluoromethoxy, —$NR^{4A}R^{4B}$ such as —NH2, —NHMethyl, —NHisopropyl, —$NR^6C(O)OR^5$, —$NR^6C(O)R^5$, —$NR^6C(O)NR^{4A}R^{4B}$, —$C(O)NR^{4A}R^{4B}$, —$C(O)R^5$ such as —COCH$_3$, —C(O)OR$^5$, and —NR$^6$S(O)$_2$R$^5$. In an embodiment R1 is optionally substituted phenyl, pyridyl, pyrrole, furan, imidazole, or thiophene.

R$^{4A}$, R$^{4B}$R$^5$ and R$^6$ are each independently selected from hydrogen, C$_{1-4}$-alkyl such as methyl, ethyl or isopropyl, or halo-C$_{1-4}$-alkyl such as trifluoromethyl, or R$^{4A}$ and R$^{4B}$ together with the nitrogen to which they are attached form a 3-7 membered cyclic amino group such as aziridine, azetidine, oxetane, pyrrolidine, piperidine, piperazine, homopiperidine, homopiperazine, morpholine, or tetrahydrofuran, optionally substituted by one or more substituents selected from: halogen such as fluoro or chloro, hydroxyl, cyano, C$_{1-4}$-alkyl such as methyl or isopropyl, halo-C$_{1-4}$-alkyl such as trifluoromethyl, C$_{1-4}$-alkoxy such as methoxy, halo-C$_{1-4}$-alkoxy such as trifluoromethoxy, —CONH$_2$, —SO$_2$NH$_2$, —NH$_2$, —NHC$_{1-4}$-alkyl, —NHhalo-C$_{1-4}$-alkyl;

The Group X

In an embodiment X is selected from —N═ or —C(R$^2$)═;

The Group R$^2$

In an embodiment R$^2$ is hydrogen, halogen such as fluoro or chloro, cyano, C$_{1-4}$-alkyl such as methyl or ethyl or isopropyl, halo-C$_{1-4}$-alkyl such as trifluoromethyl. In an embodiment R$^2$ is hydrogen.

The Group W

In an embodiment W is a phenyl ring. In an alternative embodiment W a 6-membered heterocyclic ring selected from pyridine, pyridazine, pyrazine, or pyrimidine. In an alternative embodiment W is a 5-membered ring selected from oxazole, thiazole or imidazole. Any of the aforementioned rings are optionally substituted with one or more substituents as defined in claims 1. In an embodiment W is substituted with one or more groups selected from fluoro, chloro, cyano, methyl or trifluoromethyl.

The Group W

In an embodiment V is selected from a bond, —O—, —N(R$^6$)— such as —NH— or —N(CH$_3$)—, —(C═O)—, —CONR$^6$— such as —CONH— or —CON(CH$_3$)—, —NR$^6$C(O)— such as —NHC(O)— or —N(CH$_3$)C(O)—, or —C$_{1-4}$-alkylene-, wherein the C$_{1-4}$-alkylene group is optionally substituted by halogen such as fluoro or chloro, and wherein any one of the carbon atoms of the C$_{1-4}$-alkylene group may be replaced by —O— or —N(R$^6$)— such as —CH$_2$O— in either direction or —CH$_2$—NH—; —CH$_2$—N(CH$_3$)— in either direction.

The Group R$^3$

In an embodiment R$^3$ is hydrogen. In an alternative embodiment R$^3$ an optionally substituted 3-7 membered heterocyclic ring such as aziridine, azetidine, oxetane, pyrrolidine, piperidine, piperazine, homopiperidine, homopiperazine, morpholine, or tetrahydrofuran. In an embodiment R$^3$ is an optionally substituted 3-7 membered cycloalkyl ring such as cyclopropyl, cyclopentyl or cyclohexyl. In an alternative embodiment R$^3$ is an optionally substituted 5 or 6-membered heteroaryl ring such as imidazole, phenyl, pyridine, thiophene. The optional substituents are defined in formula (I). In an embodiment any one of the rings is optionally substituted with one or more substituents selected from halogen such as fluoro or chloro, oxo, hydroxyl, cyano, C$_{1-4}$-alkyl such as methyl, ethyl, propyl, t-butyl, or isopropyl, halo-C$_{1-4}$-alkyl such as trifluoromethyl, cyano-C$_{1-4}$-alkyl, —OR$^5$ such as methoxy or trifluoromethoxy, —NR$^{4A}$R$^{4B}$ such as —NH2, NHmethyl, or morpholine or piperidine, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$.

In an embodiment R$^3$ is:

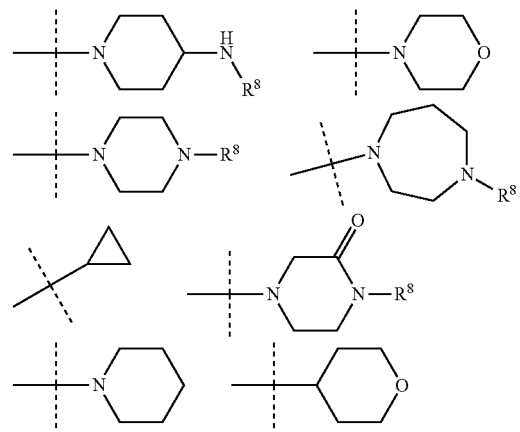

Wherein R$^8$ is selected from hydrogen, CH$_3$, —CONH$_2$, —NHCONH$_2$, —S(O)$_2$CH$_3$, —COCH$_3$, In one aspect, the invention relates to a compound of formula (I) for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders, cystic fibrosis, or inhibition of tumour growth.

In particular, it is believed that compounds of formula (I) are useful for the treatment or prevention of arthritis (such as rheumatoid arthritis, juvenile rheumatoid arthritis, osteoarthritis and psoriatic arthritis), synovitis, vasculitis, conditions associated with inflammation of the bowel (such as Crohn's disease, ulcerative colitis, inflammatory bowel disease and irritable bowel syndrome), atherosclerosis, multiple sclerosis, Alzheimer's disease, vascular dementia, pulmonary inflammatory diseases (such as asthma, chronic obstructive pulmonary disease and acute respiratory distress syndrome), fibrotic diseases (including idiopathic pulmonary fibrosis, cardiac fibrosis and systemic sclerosis (scleroderma)), inflammatory diseases of the skin (such as contact dermatitis, atopic dermatitis and psoriasis), systemic inflammatory response syndrome, sepsis, inflammatory and/or autoimmune conditions of the liver (such as autoimmune hepatitis, primary billary cirrhosis, alcoholic liver disease, sclerosing cholangitis, and autoimmune cholangitis), diabetes (type I or II) and/or the complications thereof, chronic heart failure, congestive heart failure, ischemic diseases (such as stroke and ischemia-reperfuslon injury), and myocardial infarction and/or the complications thereof.

It is believed that the compounds of the invention are especially useful for the treatment or prevention of vasculitis, including, but not limited to, giant cell arteritis, Takayasu's arteritis, Polyarteritis nodosa, Kawasaki disease, Wegener's granulomatosis, Churg-Strauss syndrome, microscopic polyangiitis, Henoch-Schönlein purpura, cryoglobulinemia, cutaneous leukocytoclastic angiitis and primary angiitis of the central nervous system.

It is also believed that the compounds of the invention are especially useful for the treatment of rheumatoid arthritis, chronic obstructive pulmonary disease or atopic dermatitis.

In view of the evidence cited in the above introduction that VAP-1 is up regulated in several cancers, including gastric cancer, melanoma, hepatoma and head and neck tumours and that mice bearing enzymatically inactive VAP-1 grow melanomas more slowly, and in view of the link between VAP-1 and angiogenesis, it is also expected that the compounds of the invention are anti-angiogenic and therefore have utility in the treatment of cancers by inhibition of tumour growth.

The invention thus includes the compounds of formula (I) above for use in the treatment or prevention of the above-mentioned conditions and diseases. The invention also includes the use of said compounds in the manufacture of a medicament for the treatment or prevention of the above-mentioned conditions and diseases. The invention furthermore includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

Compositions

A currently preferred embodiment of the invention is a pharmaceutical composition comprising a compound of formula (I), together with one or more pharmaceutically acceptable carriers and/or excipients.

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. The preparation of intermediates and compounds according to the examples of the present invention may in particular be illuminated by the following Schemes. Definitions of variables in the structures in schemes herein are commensurate with those of corresponding positions in the formulas delineated herein.

general formula (VIIa) to give amides of general formula (VIIIa) which can be cyclised to give compounds of general formula (Ia).

Optionally, the group W—V—R$^3$ can be built up sequentially using standard chemistry methodologies including amide, urea and sulphonamide formation. If required, standard protecting group strategies can be employed to facilitate the synthesis.

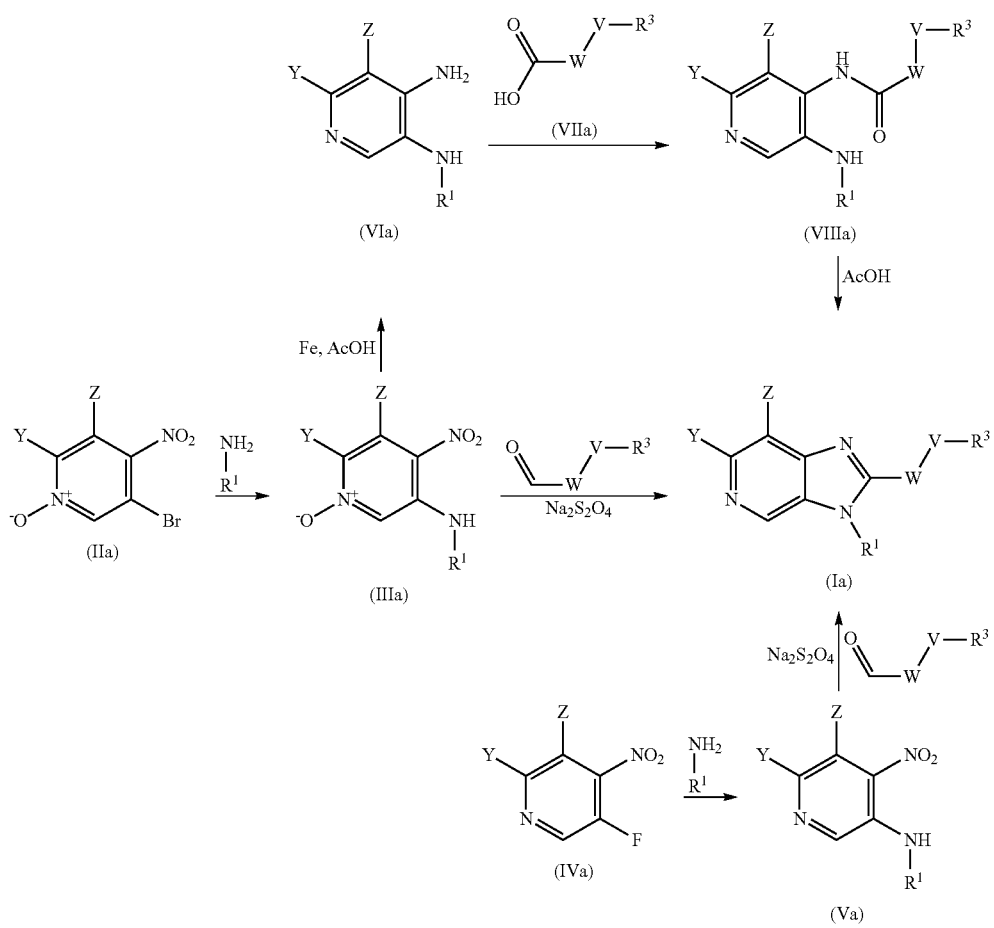

Scheme 1. General synthetic routes for preparation of compounds of formula (I) wherein X is N (i.e. compounds of general formula (Ia))

wherein V, W, X, Y, Z, R$^1$, R$^2$ and R$^3$ are as defined in formula (I);

Compounds of general formula (I) where X is N (designated compounds of general formula (Ia)), can easily be prepared by a number of alternative routes. For example, 3-bromo-4-nitropyridine N-oxides of general formula (IIa) can undergo SnAr displacement with R$^1$NH$_2$ amines to give compounds of general formula (IIIa), which can in turn be reductively cyclised to give compounds of general formula (Ia). Alternatively, 3-fluoro-4-nitropyridines of general formula (IVa) can undergo SnAr displacement with R$^1$NH$_2$ amines to give compounds of general formula (Va), which can in turn be reductively cyclised to give compounds of general formula (Ia). Alternatively, compounds of general formula (IIIa) can be reduced to pyridine-3,4-diamines of general formula (VIa). Compounds of general formula (VIa) can then undergo amide formation with carboxylic acids of Optionally, a compound of formula (Ia) can also be transformed into another compound of formula (Ia) in one or more synthetic steps.

Scheme 2. General synthetic routes for preparation of compounds of formula (I) wherein X is CR$^2$ (i.e. compounds of general formula (Ib))

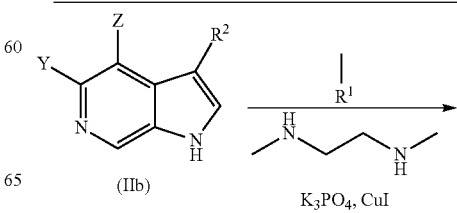

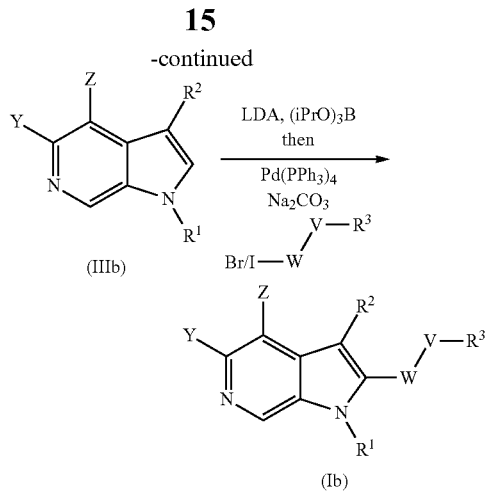

wherein V, W, X, Y, Z, $R^1$, $R^2$ and $R^3$ are as defined in formula (I);

Compounds of general formula (I) where X is $CR^2$ (designated compounds of general formula (Ib)), can easily be prepared standard means. For example, 6-azaindoles of general formula (IIb) can be N-arylated with $R^1$-I iodides to give compounds of general formula (IIIb) which can in turn be converted to compounds of general formula (Ib) by boronate formation and subsequent Suzuki coupling.

Optionally, the group $W—V—R^3$ can be built up sequentially using standard chemistry methodologies including amide, urea and sulphonamide formation. If required, standard protecting group strategies can be employed to facilitate the synthesis.

Optionally, a compound of formula (Ib) can also be transformed into another compound of formula (Ib) in one or more synthetic steps.

The following abbreviations have been used:
Ac acetyl
aq aqueous
Boc tertiary-butyloxycarbonyl
d day(s)
DCM dichloromethane
DIPEA diisopropylethylamine
DMA dimethylacetamide
DMF dimethylformamide
EDC N-(3-dimethylaminopropyl)-N'-ethylcarbodiimide
ES+ electrospray ionization
$Et_3N$ triethylamine
EtOAc ethyl acetate
EtOH ethanol
Ex Example
HBTU O-benzotriazole-N,N,N',N'-tetramethyl-uronium-hexafluoro phosphate
HPLC High Performance Liquid Chromatography
int Intermediate
LCMS Liquid Chromatography Mass Spectrometry
LDA Lithium diisopropylamide
M molar
MeCN acetonitrile
MeOH methanol
[MH]+ protonated molecular ion
min minute(s)
Rt retention time
sat saturated
TFA trifluoroacetic acid
THF tetrahydrofuran

EXAMPLES AND INTERMEDIATE COMPOUNDS

Experimental Methods

Reactions were conducted at room temperature unless otherwise specified. Microwave reactions were performed with a Biotage microwave reactor using process vials fitted with aluminium caps and septa. Preparative chromatography was performed using a Flash Master Personal system equipped with Isolute Flash II silica columns or using a CombiFlash Companion system equipped with GraceResolv silica column. Reverse Phase HPLC was performed on a Gilson system with a UV detector equipped with Phenomenex Synergi Hydro RP 150×10 mm, or YMC ODS-A 100/150×20 mm columns. The purest fractions were collected, concentrated and dried under vacuum. Compounds were typically dried in a vacuum oven at 40° C. prior to purity analysis. Compound analysis was performed by HPLC/LCMS using an Agilent 1100 HPLC system/Waters ZQ mass spectrometer connected to an Agilent 1100 HPLC system with a Phenomenex Synergi, RP-Hydro column (150×4.6 mm, 4 um, 1.5 mL per min, 30° C., gradient 5-100% MeCN (+0.085% TFA) in water (+0.1% TFA) over 7 min, 200-300 nm). The compounds prepared were named using IUPAC nomenclature.

Intermediate 1

3-[(4-Chlorophenyl)amino]-4-nitropyridin-1-ium-1-olate

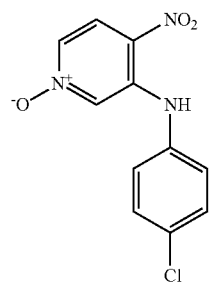

3-Bromo-4-nitropyridine N-oxide (1.00 g, 4.57 mmol) and 4-chloroaniline (1.75 g, 13.7 mmol) were dissolved in EtOH and heated at 60° C. for 18 h. The reaction mixture was cooled to 0° C. and the precipitate was collected by filtration and washed with cold EtOH to give the title compound as an orange solid (317 mg, 26.1%). LCMS (ES+): 266.1 [MH]+. HPLC: Rt 5.44 min, 99.5% purity.

Intermediates 2-3

Intermediates 2-3 were prepared similarly to Intermediate 1, by coupling of 3-bromo-4-nitropyridine N-oxide with the appropriate aniline; see Table 1 below.

TABLE 1

SnAr formation of anilines

| Int | Structure | Name | Form, Yield, LCMS, HPLC |
|---|---|---|---|
| 2 | (structure) | 3-[(4-Fluorophenyl)amino]-4-nitropyridin-1-ium-1-olate | Orange solid<br>Yield 2.66 g, 46.7%<br>LCMS (ES$^+$): 250.1 [MH]$^+$<br>HPLC: Rt 5.00 min, 97.3% purity |
| 3 | (structure) | 3-[(2-Fluoro-4-methylphenyl)amino]-4-nitropyridin-1-ium-1-olate | Orange solid<br>Yield 200 mg, 5.6%<br>LCMS (ES$^+$): 264.0 [MH]$^+$<br>HPLC: Rt 5.52 min, 93.2% purity |

Intermediate 4

N-(4-Chloro-3-fluorophenyl)-4-nitropyridin-3-amine

NaH (422 mg, 60% dispersion in mineral oil, 10.6 mmol) was suspended in THF (20 mL) and 4-chloro-3-fluoroaniline (1.54 g, 10.6 mmol) and 3-fluoro-4-nitropyridine (500 mg, 3.52 mmol) were added. The reaction mixture was stirred for 18 h, quenched with sat aq NH$_4$Cl (2 mL), and concentrated in vacuo. The residue was partitioned between water (50 mL) and DCM (50 mL) and the organic fraction was dried (MgSO$_4$) and concentrated in vacuo. The residue was purified by column chromatography to give the title compound (207 mg, 22.0%) as an orange solid. LCMS (ES$^+$): 268.0 [MH]$^+$.

Intermediate 5

N-(5-Chloropyridin-2-yl)-4-nitropyridin-3-amine

Intermediate 5 was prepared similarly to Intermediate 4, using 2-amino-5-chloropyridine instead of 4-chloro-3-fluoroaniline, to give the title compound (221 mg, 25.1%) as an orange gum. LCMS (ES$^+$): 251.1 [MH]$^+$. HPLC: Rt 5.99 min, 93.6% purity.

Intermediate 6

N-(5-Fluoropyridin-2-yl)-4-nitropyridin-3-amine

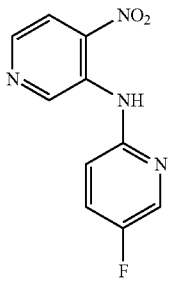 [SMILES: O=[N+]([O-])c1ccncc1Nc1ccc(F)cn1]

Intermediate 6 was prepared similarly to Intermediate 4, using 2-amino-5-fluoropyridine instead of 4-chloro-3-fluoroaniline, to give the title compound (441 mg, 53.5%) as an orange solid. LCMS (ES$^+$): 235.0 [MH]$^+$. HPLC: Rt 5.40 min, 95.2% purity.

Intermediate 7

3-N-(4-Chlorophenyl)pyridine-3,4-diamine

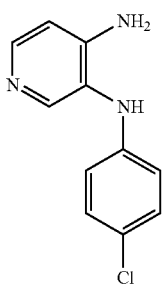 [SMILES: Nc1ccncc1Nc1ccc(Cl)cc1]

Intermediate 1 (317 mg, 1.19 mmol) was dissolved in AcOH (10 mL) and iron powder (333 mg, 5.97 mmol) was added. The reaction mixture was heated at reflux for 1 h, diluted with water (50 mL), basified with Na$_2$CO$_3$ and extracted into DCM (3×50 mL). The combined organic fractions were dried (MgSO$_4$) and concentrated in vacuo to give the title compound as a red gum (254 mg, 96.9%). LCMS (ES$^+$): 220.2 [MH]$^+$. HPLC: Rt 4.31 min, 99.5% purity.

Intermediate 8

3-N-(4-Fluorophenyl)pyridine-3,4-diamine

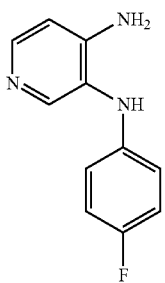 [SMILES: Nc1ccncc1Nc1ccc(F)cc1]

Intermediate 8 was prepared similarly to Intermediate 7, using Intermediate 2 instead of Intermediate 1, to give the title compound (6.33 g, 91.3%) as a brown solid. LCMS (ES$^+$): 204.1 [MH]$^+$.

Intermediate 9

Methyl 6-[(morpholin-4-yl)carbonyl]pyridine-3-carboxylate

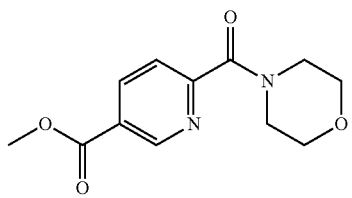 [SMILES: COC(=O)c1ccc(C(=O)N2CCOCC2)nc1]

5-(Methoxycarbonyl)pyridine-2-carboxylic acid (758 mg, 4.18 mmol) was dissolved in DMF (25 mL) and morpholine (603 uL, 5.23 mmol), Et$_3$N (2.45 mL, 16.7 mmol) and HBTU (1.67 g, 4.39 mmol) were added. The reaction mixture was stirred for 16 h and concentrated in vacuo. The residue was dissolved in EtOAc (100 mL), washed with sat aq Na$_2$CO$_3$ (100 mL), dried (MgSO$_4$) and concentrated in vacuo. The residue was purified by column chromatography to give the title compound (914 mg, 87.3%) as a yellow oil. LCMS (ES$^+$): 251.2 [MH]$^+$.

Intermediate 10

Methyl 5-[(oxan-4-yl)amino]pyrazine-2-carboxylat

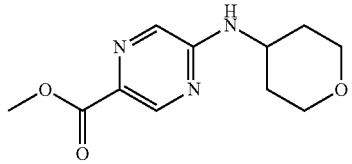 [SMILES: COC(=O)c1cnc(NC2CCOCC2)cn1]

Methyl 5-chloro-2-pyrazinecarboxylate (507 mg, 2.94 mmol), Et$_3$N (1.08 mL, 7.64 mmol) and 4-aminotetrahydropyran (0.40 mL, 3.82 mmol) were dissolved in dioxane (5 mL) and heated in a microwave reactor at 100° C. for 20 min. Water (50 mL) and brine (25 mL) were added and the reaction mixture was extracted into EtOAc (2×100 mL), dried (MgSO$_4$) and concentrated in vacuo to give the title compound (236 mg, 33.9%) as a yellow oil. LCMS (ES$^+$): 238.2 [MH]$^+$.

Intermediate 11

6-[(Morpholin-4-yl)carbonyl]pyridine-3-carboxylic Acid

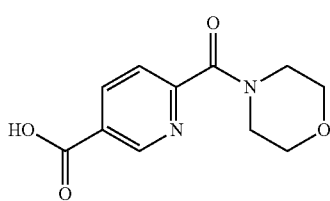 [SMILES: O=C(O)c1ccc(C(=O)N2CCOCC2)nc1]

Intermediate 9 (914 mg, 3.65 mmol) was dissolved in THF/water (24 mL, 1:1), lithium hydroxide monohydrate (184 mg, 4.38 mmol) was added and the reaction mixture was stirred for 20 min. 1M aq HCl (5 mL) was added and the reaction mixture was extracted with EtOAc (2×100 mL), dried (MgSO$_4$) and concentrated in vacuo to give the title compound (633 mg, 73.4%) as a white solid. LCMS (ES$^+$): 237.1 [MH]$^+$.

Intermediate 12

Methyl 6-(4-{[(tert-butoxy)carbonyl]amino}piperidin-1-yl)pyridine-3-carboxylate

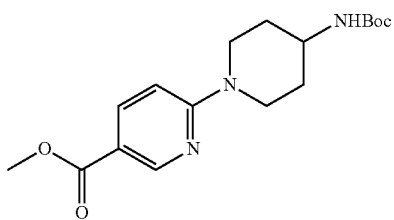 [SMILES: COC(=O)c1ccc(N2CCC(NC(=O)OC(C)(C)C)CC2)nc1]

Methyl 6-chloropyridine-3-carboxylate (1.00 g, 5.83 mmol) and 4-(N-Boc-amino)piperidine (2.33 g, 11.7 mmol) were dissolved in DMF (10 mL) and the reaction mixture was heated using a microwave reactor at 100° C. for 50 min. DIPEA (1.22 mL, 6.99 mmol) was added and the reaction mixture was heated using a microwave reactor at 100° C. for 30 min. The reaction mixture was diluted with DCM (50 mL), washed with sat aq NaHCO$_3$ (2×50 mL), dried (MgSO$_4$) and concentrated in vacuo. The residue was purified by column chromatography to give the title compound (1.66 g, 84.9%) as an off-white solid. LCMS (ES$^+$): 336.1 [MH]$^+$. HPLC: Rt 4.73 min, 98.2% purity.

Intermediate 13

Ethyl 2-[(cyclopropylmethyl)amino]pyrimidine-5-carboxylate

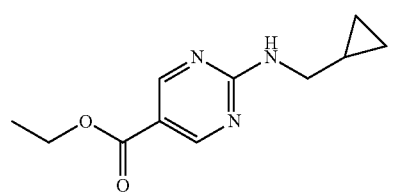 [SMILES: CCOC(=O)c1cnc(NCC2CC2)nc1]

Ethyl 2-chloropyrimidine-5-carboxylate (500 mg, 2.68 mmol), cyclopropylmethylamine (0.28 mL, 3.22 mmol) and DIPEA (0.58 mL, 3.35 mmol) were dissolved in DMF (4 mL) and the reaction mixture was heated using a microwave reactor at 100° C. for 20 min. The reaction mixture was concentrated in vacuo and the residue was partitioned between DCM (50 mL) and sat aq NaHCO$_3$ (40 mL). The organic fraction was dried (MgSO$_4$) and concentrated in vacuo to give the title compound (566 mg, 95.5%) as a yellow solid. LCMS (ES$^+$): 222.1 [MH]$^+$. HPLC: Rt 5.79 min, 92.9% purity.

Intermediate 14

Ethyl 2-(cyclopropylamino)pyrimidine-5-carboxylate

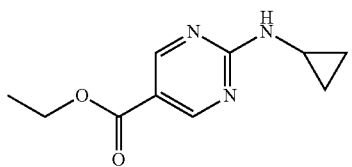

Intermediate 14 was prepared similarly to Intermediate 13, using cyclopropylamine instead of cyclopropylmethylamine, to give the title compound (526 mg, 94.7%) as a white solid. LCMS (ES$^+$): 208.1 [MH]$^+$. HPLC: Rt 4.86 min, 93.7% purity.

Intermediate 15

2-[(Oxan-4-yl)amino]pyrimidine-5-carboxylic Acid

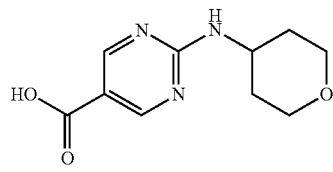

2-Chloropyrimidine-5-carboxylic acid (500 mg, 3.15 mmol), Et$_3$N (1.15 mL, 8.20 mmol) and 4-aminotetrahydropyran (335 mg, 3.31 mmol) were dissolved in dioxane (10 mL) and heated in a microwave reactor at 150° C. for 30 min. The reaction mixture was concentrated in vacuo to give the crude title compound (701 mg) as a beige solid. LCMS (ES$^+$): 224.1 [MH]$^+$.

Intermediate 16

2-(3-Oxopiperazin-1-yl)pyrimidine-5-carboxylic Acid

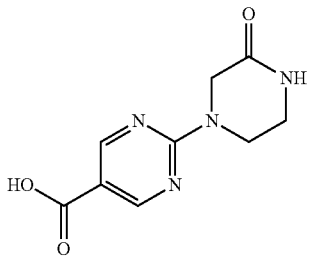 [SMILES: O=C1CN(c2ncc(C(=O)O)cn2)CCN1]

Intermediate 16 was prepared similarly to Intermediate 15, using 2-oxopiperazine instead of 4-aminotetrahydropyran, to give the crude title compound (701 mg) as a beige solid. LCMS (ES$^+$): 223.0 [MH]$^+$.

Intermediate 17

Methyl 6-(cyclopropylcarbamoyl)pyridine-3-carboxylate

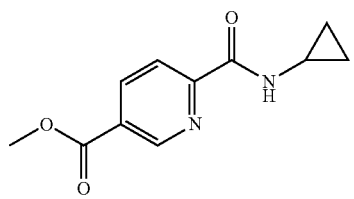 [SMILES: COC(=O)c1ccc(C(=O)NC2CC2)nc1]

5-(Methoxycarbonyl)pyridine-2-carboxylic acid (1.50 g, 8.28 mmol) was dissolved in DMF (25 mL) and cyclopropylamine (689 uL, 9.94 mmol), Et$_3$N (4.66 mL, 33.1 mmol) and HBTU (3.30 g, 8.69 mmol) were added. The reaction mixture was stirred for 3d and concentrated in vacuo. The residue was dissolved in EtOAc (100 mL), washed with sat aq Na$_2$CO$_3$ (100 mL), dried (MgSO$_4$) and concentrated in vacuo. The residue was purified by column chromatography to give the title compound (774 mg, 42.4%) as a white solid. LCMS (ES$^+$): 221.2 [MH]$^+$.

Intermediate 18

Methyl 6-methanesulfonamidopyridine-3-carboxylate

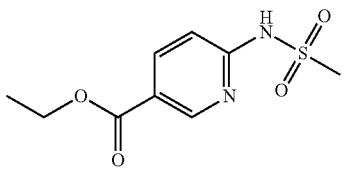 [SMILES: CCOC(=O)c1ccc(NS(C)(=O)=O)nc1]

Ethyl 6-aminopyridine-3-carboxylate (738 mg, 4.44 mmol) was dissolved in pyridine (20 mL), cooled to 0° C. and methanesulfonyl chloride (1.72 mL, 22.2 mmol) was added. The reaction mixture was stirred at room temperature for 16 h, concentrated in vacuo and partitioned between DCM (50 mL) and 1M aq citric acid (50 mL). The organic fraction was dried (MgSO$_4$) and concentrated in vacuo to give the crude title compound (1.34 g) as a brown solid. LCMS (ES$^+$): 245.1 [MH]$^+$.

Intermediate 19 tert-Butyl 4-[4-(methoxycarbonyl)-1,3-thiazol-2-yl]piperazine-1-carboxylate

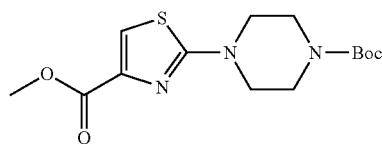 [SMILES: COC(=O)c1csc(N2CCN(C(=O)OC(C)(C)C)CC2)n1]

Methyl 2-chlorothiazole-4-carboxylate (500 mg, 2.82 mmol), N-Boc-piperazine (655 mg, 3.52 mmol) and DIPEA (736 uL, 4.22 mmol) were dissolved in DMA (10 mL) and the reaction mixture was heated in a microwave reactor at 150° C. for 45 min. The reaction mixture was partitioned between EtOAc (40 mL) and water (40 mL) and the organic fraction was washed with water (40 mL) and brine (40 mL), dried (MgSO$_4$) and concentrated in vacuo. The residue was purified by column chromatography to give the title compound as a white solid (324 mg, 35.1%). LCMS (ES$^+$): 350.1 [MNa]$^+$. HPLC: Rt 6.04 min, 100% purity.

Intermediate 20 tert-Butyl 4-[5-(methoxycarbonyl)-1,3-oxazol-2-yl]piperazine-1-carboxylate

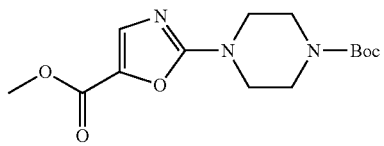

Intermediate 20 was prepared similarly to Intermediate 19, using methyl 2-chloro-1,3-oxazole-5-carboxylate instead of methyl 2-chlorothiazole-4-carboxylate, to give the title compound as a pale yellow solid (406 mg, 42.1%). LCMS (ES$^+$): 334.2 [MNa]$^+$. HPLC: Rt 5.81 min, 97.1% purity.

Intermediate 21 tert-Butyl 4-[5-(methoxycarbonyl)-1,3-thiazol-2-yl]piperazine-1-carboxylate

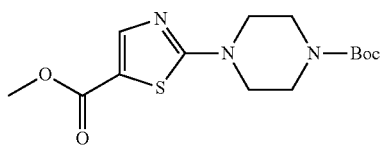 [SMILES: COC(=O)c1cnc(N2CCN(C(=O)OC(C)(C)C)CC2)o1]

Intermediate 21 was prepared similarly to Intermediate 19, using methyl 2-chlorothiazole-5-carboxylate instead of methyl 2-chlorothiazole-4-carboxylate, to give the title compound as a white solid (712 mg, 64.4%). LCMS (ES$^+$): 350.2 [MNa]$^+$, HPLC: Rt 6.34 min, 99.0% purity.

Intermediates 22-30

Intermediates 22-30 were prepared similarly to Intermediate 11, by LiOH mediated ester hydrolysis; see Table 2 below.

TABLE 2

Ester hydrolyses $$\text{R—O}\overset{\text{O}}{\underset{}{\text{—}}}\text{W—V—R}^3 \xrightarrow[\text{R = Me or Et}]{\text{LiOH}} \text{HO}\overset{\text{O}}{\underset{}{\text{—}}}\text{W—V—R}^3$$

(or Lithium salt)

| Int | Structure | Name | Intermediate(s), Form, Yield, LCMS, HPLC |
|---|---|---|---|
| 22 | 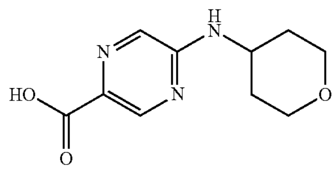 [SMILES: O=C(O)c1cnc(NC2CCOCC2)cn1] | 5-[(Oxan-4-yl)amino]pyrazine-2-carboxylic acid | From Intermediate 10<br>Yellow solid<br>Yield 222 mg, 100%<br>LCMS (ES$^+$); 224.1 [MH]$^+$ |
| 23 | 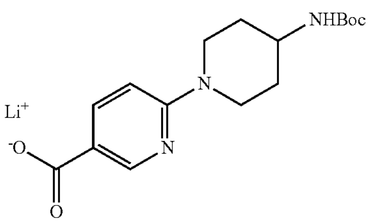 | Lithium 6-(4-{[(tert-butoxy)carbonyl]amino}piperidin-1-yl)pyridine-3-carboxylate | From Intermediate 12<br>White solid<br>Used crude<br>LCMS (ES$^+$): 322.1 [MH]$^+$<br>HPLC: Rt 4.20 min, 96.8% purity |
| 24 | 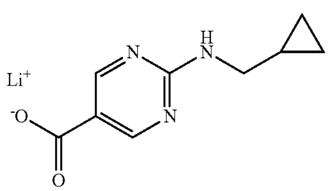 | Lithium 2-[(cyclopropylmethyl)amino]pyrimidine-5-carboxylate | From Intermediate 13<br>Off white solid<br>Used crude<br>LCMS (ES$^+$): 194.1 [MH]$^+$<br>HPLC: Rt 4.09 min, 97.4% purity |
| 25 | 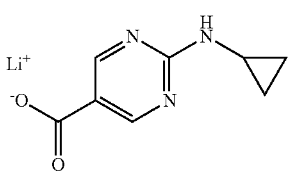 | Lithium 2-(cyclopropylamino)pyrimidine-5-carboxylate | From Intermediate 14<br>Off-white solid<br>Used crude<br>LCMS (ES$^+$): 180.1 [MH]$^+$<br>HPLC; Rt 3.23 min, 100% purity |
| 26 | 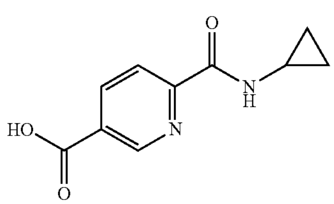 [SMILES: O=C(O)c1ccc(C(=O)NC2CC2)nc1] | 6-(Cyclopropylcarbamoyl)pyridine-3-carboxylic acid | From Intermediate 17<br>Pink solid<br>Yield 559 mg, 77.1%<br>LCMS (ES$^+$): 207.1 [MH]$^+$ |
| 27 | 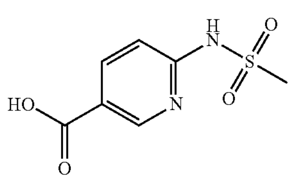 | 6-Methanesulfonamido-pyridine-3-carboxylic acid | From Intermediate 18<br>Beige solid<br>Yield 737 mg, 76.4%<br>LCMS (ES$^+$): 217.0 [MH]$^+$ |

TABLE 2-continued

Ester hydrolyses

| Int | Structure | Name | Intermediate(s), Form, Yield, LCMS, HPLC |
|---|---|---|---|
| 28 | 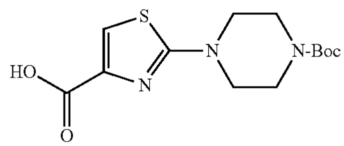 | 2-{4-[(tert-Butoxy)carbonyl]piperazin-1-yl}-1,3-thiazole-5-carboxylic acid | From Intermediate 19 white solid Yield 275 mg, 88.7% LCMS (ES+): 336.1 [MNa]+ HPLC: Rt 5.12 min, 100% purity |
| 29 | 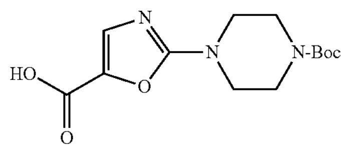 | 2-{4-[(tert-Butoxy)carbonyl]piperazin-1-yl}-1,3-oxazole-5-carboxylic acid | From Intermediate 20 White solid Yield 324 mg, 84.4% LCMS (ES+): 320.1 [MNa]+ HPLC: Rt 4.77 min, 100% purity |
| 30 | 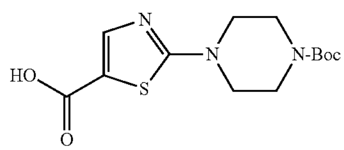 | tert-Butyl 4-[5-(methoxycarbonyl)-1,3-thiazol-2-yl]piperazine-1-carboxylate | From Intermediate 21 White solid Yield 712 mg, 64.4% LCMS (ES+): 350.2 [MNa]+ HPLC: Rt 6.34 min, 99.0% purity |

Intermediate 31

6-(3,6-Dihydro-2H-pyran-4-yl)pyridazin-3-carboxylic Acid

Intermediate 32

N-{3-[(4-Chlorophenyl)amino]pyridin-4-yl}pyridine-3-carboxamide

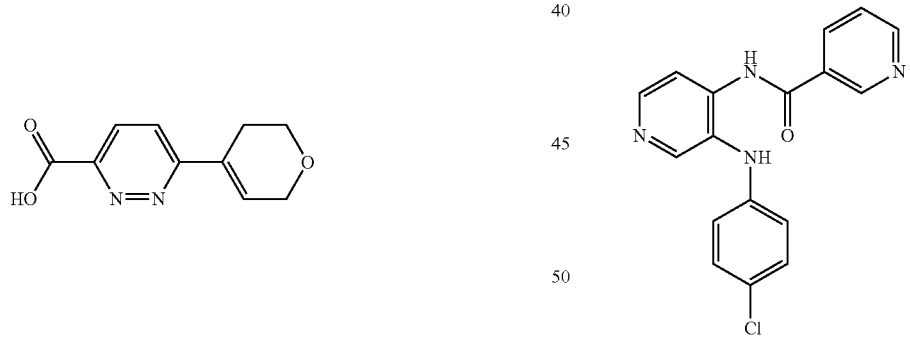

Methyl 6-chloropyridazine-3-carboxylate (1.00 g, 5.79 mmol), 4-(4,4,5,5-tetramethyl-1,3,2-dioxaborolan-2-yl)-3,6-dihydro-2H-pyran (1.22 g, 5.79 mmol), Pd(PPh3)4 (536 mg, 0.44 mmol) and Cs2CO3 (3.40 g, 10.4 mmol) were suspended in dioxane (8 mL) and water (8 mL) and heated in a microwave reactor at 125° C. for 30 min. 1M aq HCl (10 mL) was added, the precipitate was removed by filtration and the filtrate was concentrated in vacuo. The residue was passed through a silica pad eluting with 30% MeOH in DCM and concentrated in vacuo to give the title compound as a white solid (946 mg, 79.2%). LCMS (ES+): 207.1 [MH]+. HPLC: Rt 3.30 min, 49.9% purity.

Intermediate 7 (234 mg, 1.07 mmol), pyridine-4-carboxylic acid (393 mg, 3.20 mmol) and DIPEA (741 uL, 4.26 mmol) were dissolved in DMF (10 mL) and EDC (613 mg, 3.20 mmol) was added. The reaction mixture was stirred for 18 h and further pyridine-3-carboxylic acid (393 mg, 3.20 mmol) and EDC (613 mg, 3.20 mmol) were added. The reaction mixture was stirred for 5 h, diluted with 1M aq Na2CO3 (50 mL) and extracted into DCM (3×50 mL). The combined organic fractions were dried (MgSO4) and concentrated in vacuo. The residue was purified by column chromatography to give the title compound as a red gum (297 mg, 85.8%). LCMS (ES+): 325.1 [MH]+. HPLC: Rt 4.08 min, 99.0% purity.

Intermediates 33-51

Intermediates 33-51 were prepared similarly to Intermediate 32, by coupling of Intermediates 7 or 8 with the appropriate carboxylic acid; see Table 3 below.

TABLE 3

Amide couplings

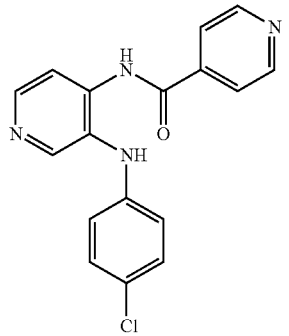 [SMILES: O=C(Nc1ccncc1Nc1ccc(Cl)cc1)c1ccncc1]

| Int | Structure | Name | Intermediate(s), Form, Yield, LCMS, HPLC |
|---|---|---|---|
| 33 | 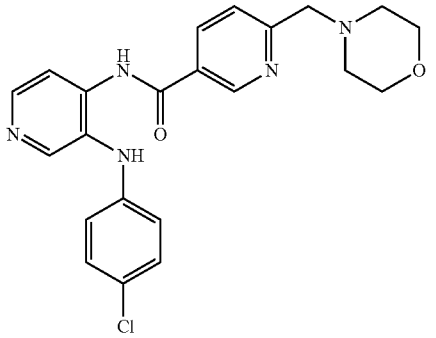 [SMILES: O=C(Nc1ccncc1Nc1ccc(Cl)cc1)c1ccc(CN2CCOCC2)nc1] | N-{3-[(4-Chlorophenyl)amino]pyridin-4-yl}pyridine-3-carboxamide | From Intermediate 7<br>Yellow solid<br>Yield 219 mg, 58.3%<br>LCMS (ES$^+$): 325.2 [MH]$^+$<br>HPLC: Rt 4.18 min, 95.8% purity |
| 34 | 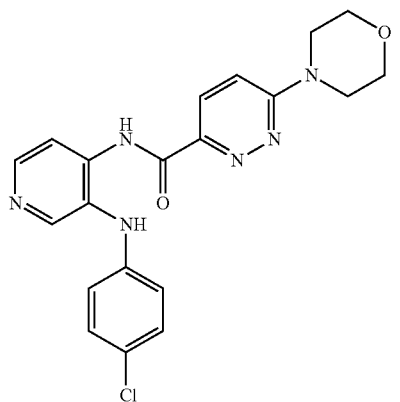 | N-{3-[(4-Chlorophenyl)amino]pyridin-4-yl}-6-(morpholin-4-ylmethyl)pyridine-3-carboxamide | From Intermediate 7<br>Yellow solid<br>Yield 282 mg, 21.1%<br>LCMS (ES$^+$); 424.1 [MH]$^+$ |
| 35 | 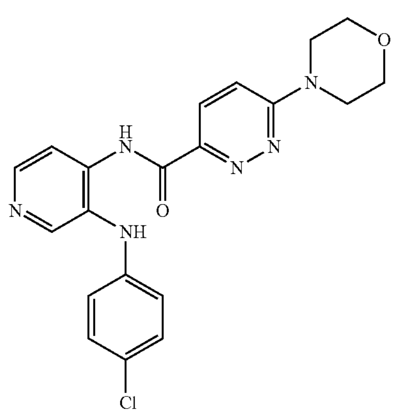 [SMILES: O=C(Nc1ccncc1Nc1ccc(Cl)cc1)c1ccc(N2CCOCC2)nn1] | N-{3-[(4-Chlorophenyl)amino]pyridin-4-yl}-6-(morpholin-4-yl)pyridazine-3-carboxamide | From Intermediate 7<br>Yellow solid<br>Yield 500 mg, 53.2%<br>LCMS (ES$^+$): 411.0 [MH]$^+$ |

TABLE 3-continued

Amide couplings

| Int | Structure | Name | Intermediate(s), Form, Yield, LCMS, HPLC |
|---|---|---|---|
| 36 | 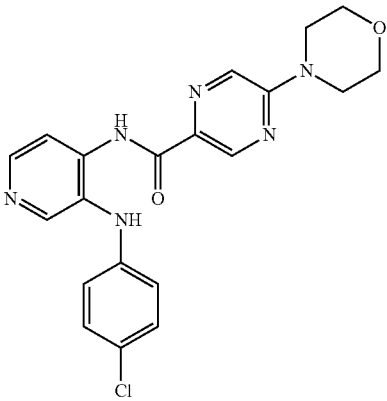 [SMILES: O=C(Nc1ccncc1Nc1ccc(Cl)cc1)c1cnc(N2CCOCC2)cn1] | N-{3-[(4-Chlorophenyl)amino]pyridin-4-yl}-5-(morpholin-4-yl)pyridazine-2-carboxamide | From Intermediate 7<br>Yellow oil<br>Yield 633 mg, 73.5%<br>LCMS (ES$^+$): 411.0 [MH]$^+$ |
| 37 | 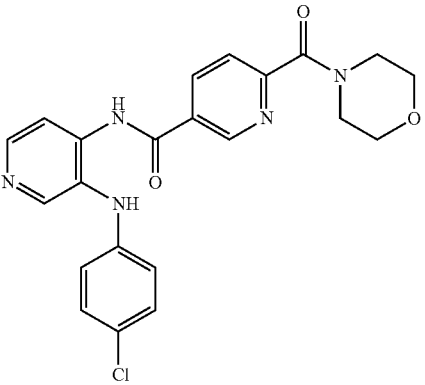 [SMILES: O=C(Nc1ccncc1Nc1ccc(Cl)cc1)c1ccc(C(=O)N2CCOCC2)nc1] | N-{3-[(4-Chlorophenyl)amino]pyridin-4-yl}-6-[(morpholin-4-yl)carbonyl]pyridine-3-carboxamide | From Intermediates 7 and 11<br>Yellow oil<br>Yield 437 mg, 54.9%<br>LCMS (ES$^+$): 438.0 [MH]$^+$ |
| 38 | 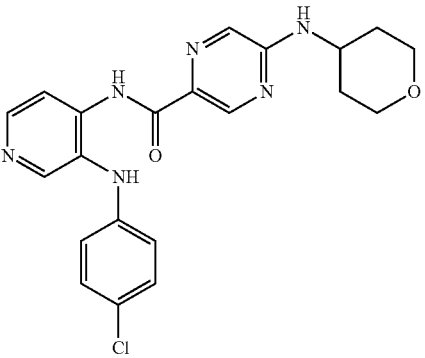 [SMILES: O=C(Nc1ccncc1Nc1ccc(Cl)cc1)c1cnc(NC2CCOCC2)cn1] | N-{3-[(4-Chlorophenyl)amino]pyridin-4-yl}-5-[(oxan-4-yl)amino]pyrazine-2-carboxamide | From Intermediates 7 and 22<br>Yellow oil<br>Yield 174 mg, 45.8%<br>LCMS (ES$^+$): 425.1 [MH]$^+$ |

TABLE 3-continued

Amide couplings

| Int | Structure | Name | Intermediate(s), Form, Yield, LCMS, HPLC |
|---|---|---|---|
| 39 | 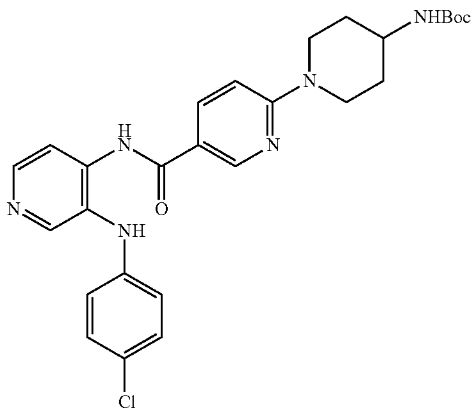 [SMILES: CC(C)(C)OC(=O)NC1CCN(c2ccc(C(=O)Nc3ccncc3Nc3ccc(Cl)cc3)cn2)CC1] | tert-Butyl N-{1-[5-({3-[(4-chlorophenyl)amino]pyridin-4-yl}carbamoyl)pyridin-2-yl]piperidin-4-yl}carbamate | From Intermediates 7 and 23<br>Off white solid<br>Yield 954 mg, 78.4% LCMS (ES$^+$): 523.1 [MH]$^+$ HPLC: Rt 5.16 min, 97.8% purity |
| 40 | 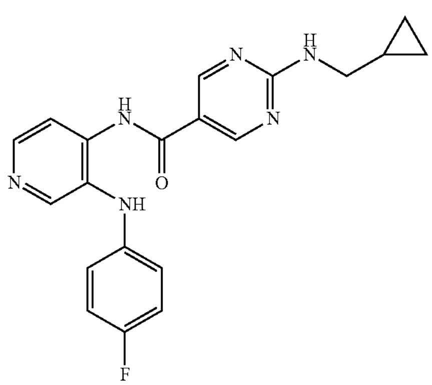 [SMILES: O=C(Nc1ccncc1Nc1ccc(F)cc1)c1cnc(NCC2CC2)nc1] | 2-[(Cyclopropylmethyl)amino]-N-{3-[(4-fluorophenyl)amino]pyridin-4-yl}pyrimidine-5-carboxamide | From Intermediates 8 and 24<br>Yellow solid<br>Yield 312 mg, 32.3%<br>LCMS (ES$^+$): 379.2 [MH]$^+$<br>HPLC: Rt 4.91 min, 96.3% purity |
| 41 | 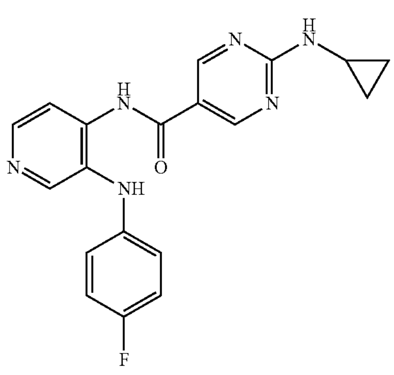 [SMILES: O=C(Nc1ccncc1Nc1ccc(F)cc1)c1cnc(NC2CC2)nc1] | 2-(Cyclopropylamino)-N-{3-[(4-fluorophenyl)amino]pyridin-4-yl}pyrimidine-5-carboxamide | From Intermediates 8 and 25<br>Yellow solid<br>Yield 859 mg, 71.2%<br>LCMS (ES$^+$): 365.1 [MH]$^+$<br>HPLC: Rt 4.41 min, 68.3% purity |

TABLE 3-continued

Amide couplings

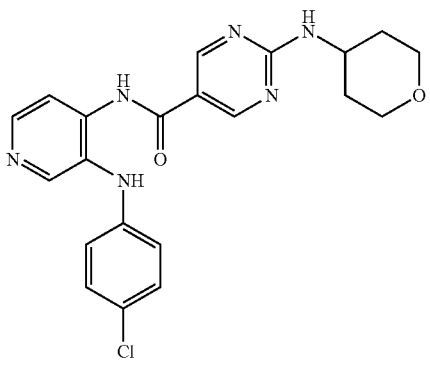 [SMILES: O=C(Nc1ccncc1Nc1ccc(Cl)cc1)c1cnc(NC2CCOCC2)nc1]

| Int | Structure | Name | Intermediate(s), Form, Yield, LCMS, HPLC |
|---|---|---|---|
| 42 | 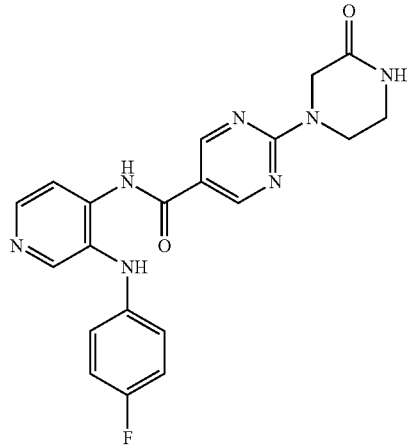 [SMILES: O=C1CN(c2ncc(C(=O)Nc3ccncc3Nc3ccc(F)cc3)cn2)CCN1] | N-{3-[(4-Chlorophenyl)amino]pyridin-4-yl}-2-[(oxan-4-yl)amino]pyrimidine-5-carboxamide | From Intermediates 7 and 15<br>Yellow oil<br>Yield 917 mg, 86.3%<br>LCMS (ES$^+$): 425.1 [MH]$^+$ |
| 43 | 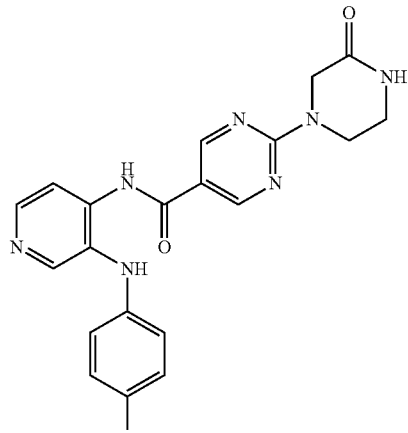 | N-{3-[(4-Fluorophenyl)amino]pyridin-4-yl}-2-(3-oxopiperazin-1-yl)pyrimidine-5-carboxamide | From Intermediates 8 and 16<br>Yellow gum<br>Used crude (1.88 g)<br>LCMS (ES$^+$): 408.1 [MH]$^+$ |
| 44 | 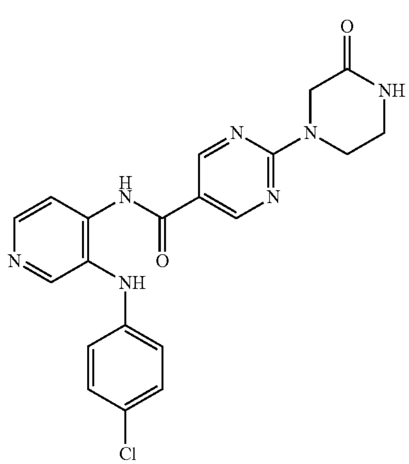 [SMILES: O=C1CN(c2ncc(C(=O)Nc3ccncc3Nc3ccc(Cl)cc3)cn2)CCN1] | N-{3-[(4-Chlorophenyl)amino]pyridin-4-yl}-2-(3-oxopiperazin-1-yl)pyrimidine-5-carboxamide | From Intermediates 7 and 18<br>Yellow solid<br>Yield 712 mg, 58.8%<br>LCMS (ES$^+$): 424.1 [MH]$^+$ |

TABLE 3-continued

Amide couplings

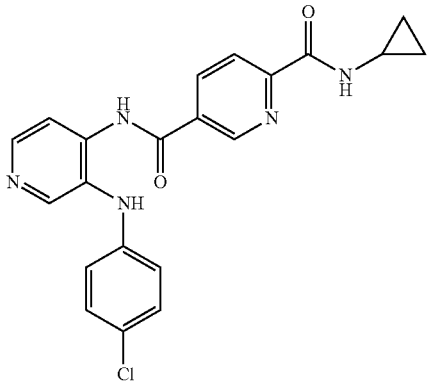 [SMILES: O=C(Nc1ccncc1Nc1ccc(Cl)cc1)c1ccc(C(=O)NC2CC2)nc1]

| Int | Structure | Name | Intermediate(s), Form, Yield, LCMS, HPLC |
|---|---|---|---|
| 45 | 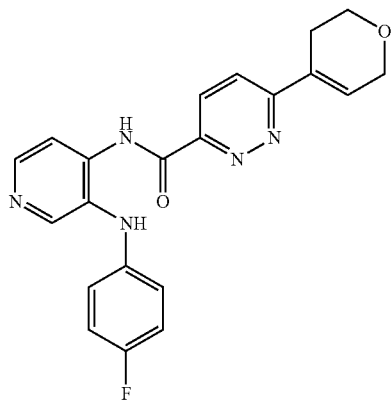 [SMILES: O=C(Nc1ccncc1Nc1ccc(F)cc1)c1ccc(C2=CCOCC2)nn1] | 5-N-{3-[(4-Chlorophenyl)amino]pyridin-4-yl}-2-N-cyclopropylpyridine-2,5-dicarboxamide | From Intermediates 7 and 26<br>Yellow solid<br>Yield 790 mg, 84.9%<br>LCMS (ES$^+$): 408.1 [MH]$^+$ |
| 46 | 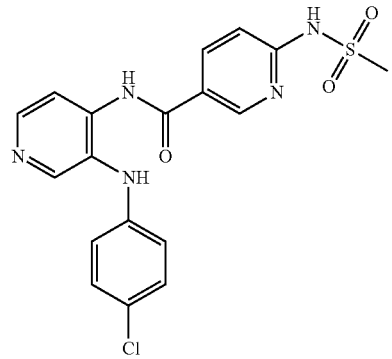 | 6-(3,6-Dihydro-2H-pyran-4-yl)-N-{3-[(4-fluorophenyl)amino]pyridin-4-yl}pyridazine-3-carboxamide | From Intermediates 8 and 31<br>Orange semi-solid<br>Yield 467 mg, 54.7%<br>LCMS (ES$^+$): 392.2 [MH]$^+$<br>HPLC: Rt 4.87 min, 50.9% purity |
| 47 | 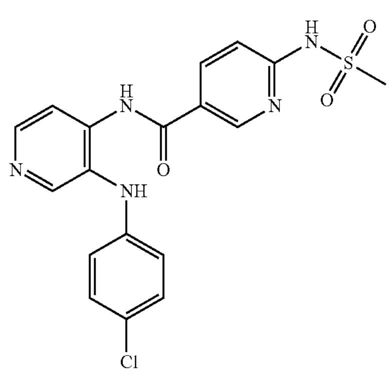 [SMILES: CS(=O)(=O)Nc1ccc(C(=O)Nc2ccncc2Nc2ccc(Cl)cc2)cn1] | N-{3-[(4-Chlorophenyl)amino]pyridin-4-yl}-6-methanesulfonamidopyridine-3-carboxamide | From Intermediates 7 and 27<br>Beige solid<br>Yield 348 mg, 40.6%<br>LCMS (ES$^+$): 418.0 [MH]$^+$ |

TABLE 3-continued

Amide couplings

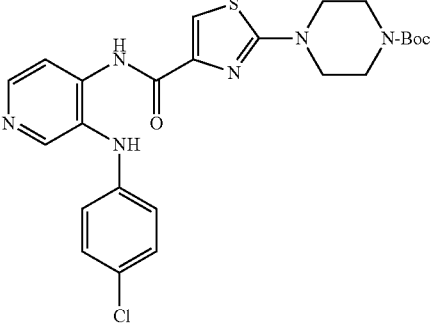

| Int | Structure | Name | Intermediate(s), Form, Yield, LCMS, HPLC |
|---|---|---|---|
| 48 | 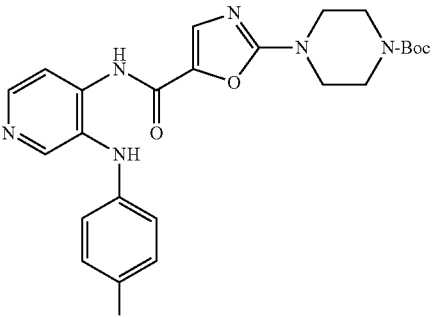 | tert-Butyl 4-[4-({3-[(4-chlorophenyl)amino]pyridin-4-yl}carbamoyl)-1,3-thiazol-2-yl]piperazine-1-carboxylate | From Intermediates 7 and 28<br>White solid<br>Yield 302 mg, 66.8%<br>LCMS (ES$^+$): 515.0 [MH]$^+$<br>HPLC: Rt 6.37 min, 94.2% purity |
| 49 | 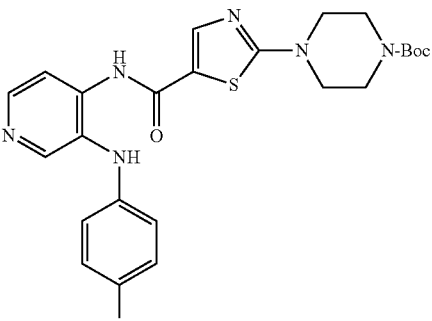 | tert-Butyl 4-[5-({3-[(4-chlorophenyl)amino]pyridin-4-yl}carbamoyl)-1,3-oxazol-yl]piperazine-1-carboxylate | From Intermediates 7 and 29<br>Orange solid<br>Yield 602 mg, 100%<br>LCMS (ES$^+$): 499.0 [MH]$^+$<br>HPLC: Rt 5.76 min, 76.4% purity |
| 50 | 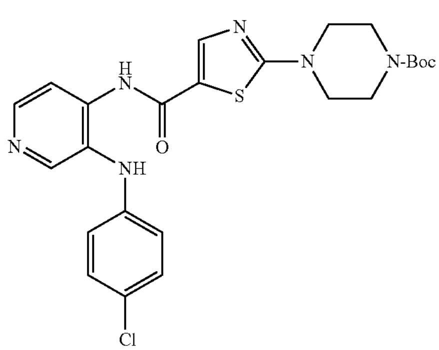 | tert-Butyl 4-[5-({3-[(4-chlorophenyl)amino]pyridin-4-yl}carbamoyl)-1,3-thiazol-2-yl]piperazine-1-carboxylate | From Intermediates 7 and 30<br>White solid<br>Yield 656 mg, 97.9%<br>LCMS (ES$^+$): 336.1 [MNa]$^+$<br>HPLC: Rt 5.19 min, 99.3% purity |

TABLE 3-continued

Amide couplings

| Int | Structure | Name | Intermediate(s), Form, Yield, LCMS, HPLC |
|---|---|---|---|
| 51 | 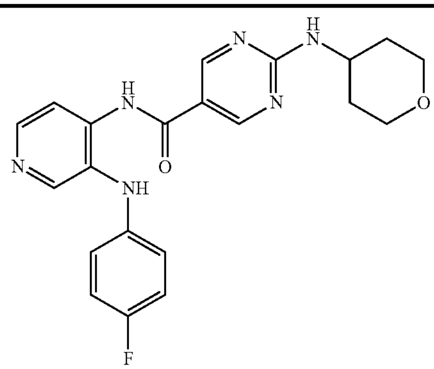 | N-{3-[(4-Fluorophenyl)amino]pyridin-4-yl}-2-[(oxan-4-yl)amino]pyrimidine-5-carboxamide | From Intermediates 8 and 15<br>Beige solid<br>Yield 593 mg, 59.0%<br>LCMS (ES$^+$): 409.1 [MH]$^+$ |

Intermediate 52

1-{5-[3-(4-Fluorophenyl)-3H-imidazo[4,5-c]pyridin-2-yl]pyridin-2-yl}piperazine Trihydrochloride

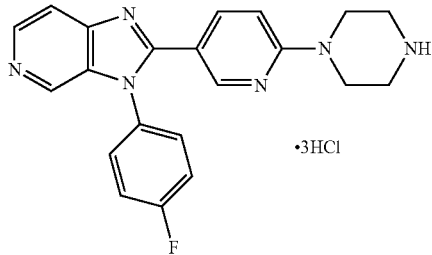 [SMILES: Fc1ccc(-n2c(-c3ccc(N4CCNCC4)nc3)nc3ccncc32)cc1]

Intermediate 52 was prepared similarly to Example 27, using Intermediate 2 instead of Intermediate 1, to give the title compound (684 mg, 100%) as a white solid. LCMS (ES+): 375.1 [MH]$^+$.

Intermediate 53

N-{3-[(4-Fluorophenyl)amino]pyridin-4-yl}-6-(oxan-4-yl)pyridazine-3-carboxamide

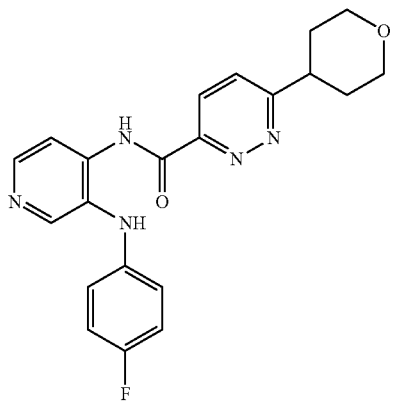 [SMILES: O=C(Nc1ccncc1Nc1ccc(F)cc1)c1ccc(C2CCOCC2)nn1]

Intermediate 46 (220 mg, 0.56 mmol) was dissolved in MeOH (10 mL), Pd/C (cat) was added and the reaction mixture was stirred under hydrogen for 2 h. The reaction mixture was filtered through Celite and concentrated in vacuo to give the crude title compound which was used without purification. LCMS (ES$^+$): 394.2 [MH]$^+$.

Intermediate 54

2-Chloro-5-[3-(4-fluorophenyl)-3H-imidazo[4,5-c]pyridin-2-yl]pyridine

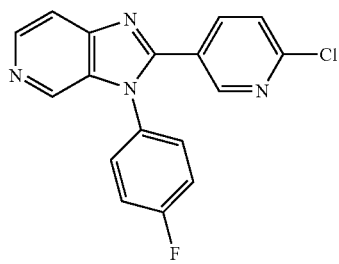 [SMILES: Fc1ccc(-n2c(-c3ccc(Cl)nc3)nc3ccncc32)cc1]

Intermediate 2 (1.00 g, 4.01 mmol) and 2-chloro-5-pyridinecarboxaldehyde (682 mg, 4.82 mmol) were dissolved in EtOH (8 mL) and Na$_2$S$_2$O$_4$ (2.79 g, 16.1 mmol) was added. The reaction mixture was heated in a microwave reactor at 160° C. for 1 h, diluted with water (25 mL) and NaHCO$_3$ (25 mL) and extracted into DCM (3×50 mL). The combined organic fractions were dried (MgSO$_4$) and concentrated in vacuo. The residue was purified by column chromatography to give the title compound (375 mg, 28.8%) as a yellow oil. LCMS (ES$^+$): 325.1 [MH]$^+$.

Intermediate 55

1-{5-[3-(4-fluorophenyl)-3H-imidazo[4,5-c]pyridin-2-yl]pyridin-2-yl}-1,4-diazepane

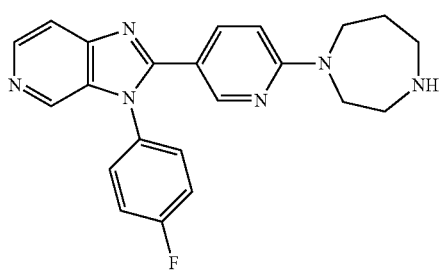 [SMILES: Fc1ccc(-n2c(-c3ccc(N4CCCNCC4)nc3)nc3ccncc32)cc1]

Intermediate 54 (375 mg, 1.15 mmol) and homopiperazine (578 mg, 5.77 mmol) were dissolved in DMA (6 mL) and the reaction mixture was heated in a microwave reactor at 180° C. for 30 min and concentrated in vacuo. The residue was partitioned between DCM (50 mL) and sat aq Na$_2$CO$_3$ (50 mL) and the organic fraction dried (MgSO$_4$) and concentrated in vacuo to give the title compound (410 mg, 91.5%) as a red oil. LCMS (ES$^+$): 389.2 [MH]$^+$.

Intermediate 56

1-(4-Chlorophenyl)-1H-pyrrolo[2,3-c]pyridine

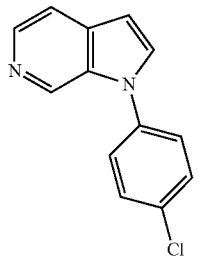 [SMILES: Clc1ccc(-n2ccc3ccncc32)cc1]

6-Azaindole (5.00 g, 42.3 mmol) was dissolved in DMF (150 mL) under nitrogen and 1-chloro-4-iodo-benzene (12.2 g, 50.8 mmol), N,N'-dimethylethylenediamine (911 uL, 8.46 mmol), K$_3$PO$_4$ (18.9 g, 88.9 mmol) and CuI (806 mg, 4.23 mmol) were added. The reaction mixture was heated at 150° C. for 18 h. The reaction mixture was filtered and the filtrate was concentrated in vacuo. The residue was suspended in 1M aq Na$_2$CO$_3$ (250 mL) and extracted into DCM (2×250 mL). The combined organic fractions were dried (MgSO$_4$) and concentrated in vacuo. The residue was purified by column chromatography to give the title compound as a yellow solid (8.58 g, 88.6%). LCMS (ES$^+$): 229.1 [MH]$^+$. HPLC: Rt 4.48 min, 98.6% purity.

Intermediate 57

1-(4-Iodobenzoyl)-4-methylpiperazine

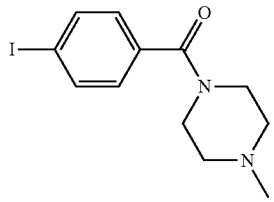 [SMILES: CN1CCN(C(=O)c2ccc(I)cc2)CC1]

4-Iodobenzoic acid (500 mg, 2.02 mmol) and DMF (50 uL) were dissolved in DCM (24 mL), oxalyl chloride (0.18 mL, 2.12 mmol) was added drop-wise and the reaction mixture was stirred for 30 min. DIPEA (0.42 mL, 2.42 mmol) and a solution of N-methylpiperazine (222 mg, 2.22 mmol) in DCM (1 mL) were added and the reaction mixture was stirred for 30 min, washed with sat aq NaHCO$_3$ (2×75 mL), dried (MgSO$_4$) and concentrated in vacuo to give the title compound (660 mg, 99.2%) as a yellow solid. LCMS (ES$^+$): 331.0 [MH]$^+$. HPLC: Rt 4.05 min, 99.6% purity.

Example 1

3-[3-(4-Chlorophenyl)-3H-imidazo[4,5-c]pyridin-2-yl]pyridine

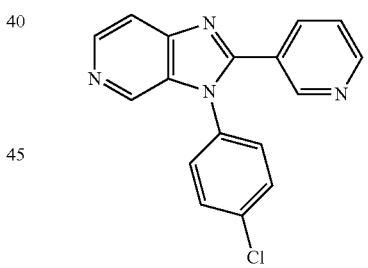

Intermediate 32 (297 mg, 0.91 mmol) was dissolved in AcOH (5 mL) and heated using a microwave reactor at 100° C. for 15 min, diluted with water (50 mL), basified with Na$_2$CO$_3$ and extracted into DCM (3×50 mL). The combined organic fractions were dried (MgSO$_4$) and concentrated in vacuo. The residue was purified by column chromatography to give the title compound as a white solid (139 mg, 49.5%). LCMS (ES$^+$): 307.1 [MH]$^+$. HPLC: Rt 4.22 min, 99.8% purity.

Examples 2-20

Examples 2-20 were prepared similarly to Example 1, by cyclisation of Intermediates 33-45, 47-51 and 53; see Table 4 below.

TABLE 4

Cyclisation of Intermediates 33-45, 47-51 and 53

| Ex | Structure | Name | Intermediate(s), Form, Yield, LCMS, HPLC |
|---|---|---|---|
| 2 | 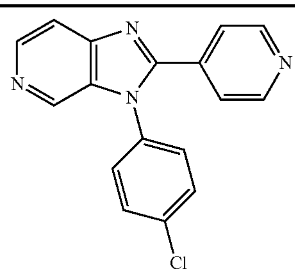 | 4-[3-(4-Chlorophenyl)-3H-imidazo[4,5-c]pyridin-2-yl]pyridine | From Intermediate 33<br>Light pink solid<br>Yield 109 mg, 52.7%<br>LCMS (ES+): 307.2 [MH]+<br>HPLC: Rt 3.90 min, 99.8% purity |
| 3 | 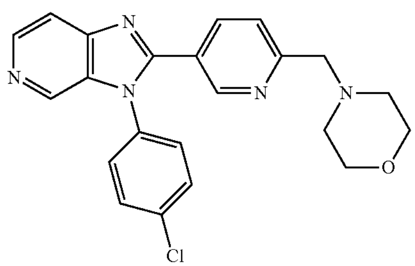 [SMILES: Clc1ccc(-n2c(-c3ccc(CN4CCOCC4)nc3)nc3ccncc32)cc1] | 4-({5-[3-(4-Chlorophenyl)-3H-imidazo[4,5-c]pyridin-2-yl]pyridin-2-yl}methyl)morpholine | From Intermediate 34<br>While solid<br>Yield 105 mg, 38.6%<br>LCMS (ES+): 406.0 [MH]+<br>HPLC: Rt 3.65 min, 100% purity |
| 4 | 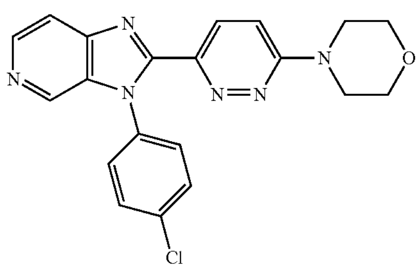 [SMILES: Clc1ccc(-n2c(-c3ccc(N4CCOCC4)nn3)nc3ccncc32)cc1] | 4-{6-[3-(4-Chlorophenyl)-3H-imidazo[4,5-c]pyridin-2-yl]pyridazin-3-yl}morpholine | From Intermediate 35<br>White solid<br>Yield 89.9 mg, 18.8%<br>LCMS (ES+): 393.1 [MH]+<br>HPLC: Rt 4.71 min, 98.4% purity |
| 5 | 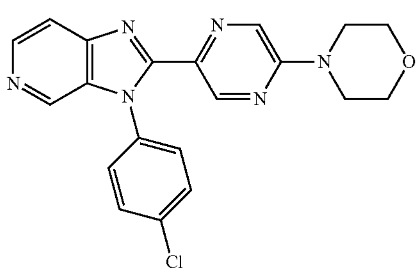 [SMILES: Clc1ccc(-n2c(-c3cnc(N4CCOCC4)cn3)nc3ccncc32)cc1] | 4-{5-[3-(4-Chlorophenyl)-3H-imidazo[4,5-c]pyridin-2-yl]pyrazin-2-yl}morpholine | From Intermediate 36<br>White solid<br>Yield 114 mg, 18.9%<br>LCMS (ES+): 393.1 [MH]+<br>HPLC: Rt 4.79 min, 100% purity |
| 6 | 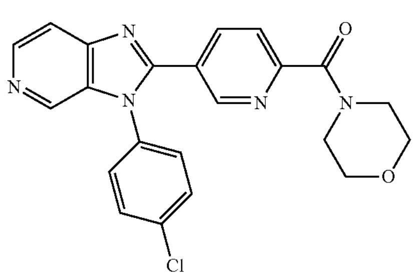 [SMILES: O=C(c1ccc(-c2nc3ccncc3n2-c2ccc(Cl)cc2)cn1)N1CCOCC1] | 4-({5-[3-(4-Chlorophenyl)-3H-imidazo[4,5-c]pyridin-2-yl]pyridin-2-yl}carbonyl)morpholine | From Intermediate 37<br>White solid<br>Yield 170 mg, 40.5%<br>LCMS (ES+): 420.1 [MH]+<br>HPLC: Rt 5.15 min, 100% purity |

TABLE 4-continued

Cyclisation of Intermediates 33-45, 47-51 and 53

| Ex | Structure | Name | Intermediate(s), Form, Yield, LCMS, HPLC |
|---|---|---|---|
| 7 | 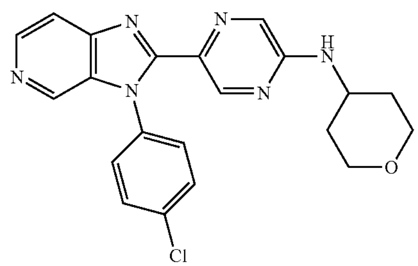 [SMILES: Clc1ccc(-n2c(-c3cnc(NC4CCOCC4)cn3)nc3ccncc32)cc1] | 5-[3-(4-Chlorophenyl)-3H-imidazo[4,5-c]pyridin-2-yl]-N-(oxan-4-yl)pyrazin-2-amine | From Intermediate 38<br>Yellow solid<br>Yield 50.0 mg, 30.0%<br>LCMS (ES$^+$): 407.1 [MH]$^+$<br>HPLC: Rt 4.86 min, 100% purity |
| 8 | 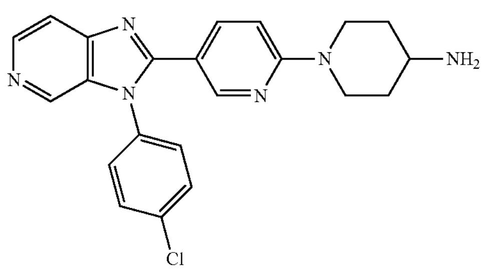 [SMILES: NC1CCN(c2ccc(-c3nc4ccncc4n3-c3ccc(Cl)cc3)cn2)CC1] | 1-{5-[3-(4-Chlorophenyl)-3H-imidazo[4,5-c]pyridin-2-yl]pyridin-2-yl}piperidin-4-amine | From Intermediate 39<br>White solid<br>Yield 24.2 mg, 38.7%<br>LCMS (ES$^+$): 405.0 [MH]$^+$<br>HPLC: Rt 3.52 min, 100% purity |
| 9 | 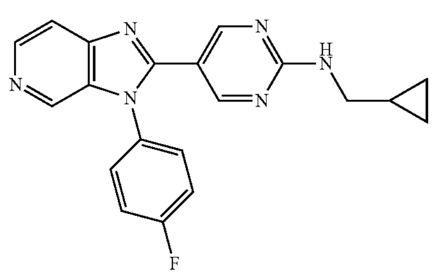 [SMILES: Fc1ccc(-n2c(-c3cnc(NCC4CC4)nc3)nc3ccncc32)cc1] | N-(Cyclopropylmethyl)-5-[3-(4-fluorophenyl)-3H-imidazo[4,5-c]pyridin-2-yl]pyrimidin-2-amine | From Intermediate 40<br>White solid<br>Yield 24.6 mg, 8.3%<br>LCMS (ES$^+$): 361.2 [MH]$^+$<br>HPLC: Rt 5.01 min, 97.0% purity |
| 10 | 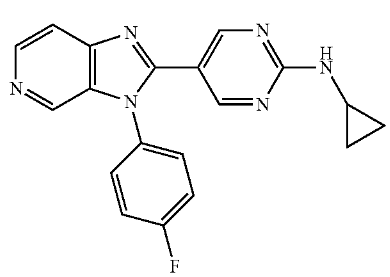 [SMILES: Fc1ccc(-n2c(-c3cnc(NC4CC4)nc3)nc3ccncc32)cc1] | N-Cyclopropyl-5-[3-(4-fluorophenyl)-3H-imidazo[4,5-c]pyridin-2-yl]pyrimidin-2-amine | From Intermediate 41<br>White solid<br>Yield 30.9 mg, 4.9%<br>LCMS (ES$^+$): 347.1 [MH]$^+$<br>HPLC: Rt 4.46 min, 99.2% purity |

TABLE 4-continued

Cyclisation of Intermediates 33-45, 47-51 and 53

| Ex | Structure | Name | Intermediate(s), Form, Yield, LCMS, HPLC |
|---|---|---|---|
| 11 | (structure with imidazo[4,5-c]pyridine, pyrimidine, tetrahydropyran-amine, 4-chlorophenyl; ·2TFA) | 5-[3-(4-Chlorophenyl)-3H-imidazo[4,5-c]pyridin-2-yl]-N-(oxan-4-yl)pyrimidin-2-amine; bis(trifluoroacetic acid) | From Intermediate 42<br>White solid<br>Yield 73.8 mg, 5.4%<br>LCMS (ES$^+$): 407.1 [MH]$^+$<br>HPLC: Rt 4.76 min, 100% purity |
| 12 | (structure with imidazo[4,5-c]pyridine, pyrimidine, piperazin-2-one, 4-fluorophenyl) | 4-{5-[3-(4-Fluorophenyl)-3H-imidazo[4,5-c]pyridin-2-yl]pyrimidin-2-yl}piperazin-2-one | From Intermediate 43<br>White solid<br>Yield 104 mg, 9.3%<br>LCMS (ES$^+$): 390.1 [MH]$^+$<br>HPLC: Rt 4.01 min, 100% purity |
| 13 | (structure with imidazo[4,5-c]pyridine, pyrimidine, piperazin-2-one, 4-chlorophenyl) | 4-{5-[3-(4-Chlorophenyl)-3H-imidazo[4,5-c]pyridin-2-yl]pyrimidin-2-yl}piperazin-2-one | From Intermediate 44<br>White solid<br>Yield 97.1 mg, 14.2%<br>LCMS (ES$^+$): 406.0 [MH]$^+$<br>HPLC: Rt 4.25 min, 99.5% purity |
| 14 | (structure with imidazo[4,5-c]pyridine, pyridine-2-carboxamide, cyclopropyl, 4-chlorophenyl) | 5-[3-(4-Chlorophenyl)-3H-imidazo[4,5-c]pyridin-2-yl]-N-cyclopropylpyridine-2-carboxamide | From Intermediate 45<br>White solid<br>Yield 100 mg, 13.3%<br>LCMS (ES$^+$): 390.0 [MH]$^+$<br>HPLC: Rt 4.81 min, 100% purity |

TABLE 4-continued

Cyclisation of Intermediates 33-45, 47-51 and 53

| Ex | Structure | Name | Intermediate(s), Form, Yield, LCMS, HPLC |
|---|---|---|---|
| 15 | 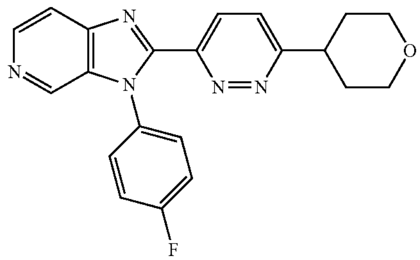 [SMILES: Fc1ccc(-n2c(-c3ccc(C4CCOCC4)nn3)nc3ccncc32)cc1] | 6-(3,6-Dihydro-2H-pyran-4-yl)-N-{3-[(4-fluorophenyl)amino]pyridin-4-yl}pyridazine-3-carboxamide | From Intermediate 53<br>Off white solid<br>Yield 14.0 mg, 6.6%<br>LCMS (ES$^+$): 376.2 [MH]$^+$<br>HPLC: Rt 4.37 min, 98.4% purity |
| 16 | 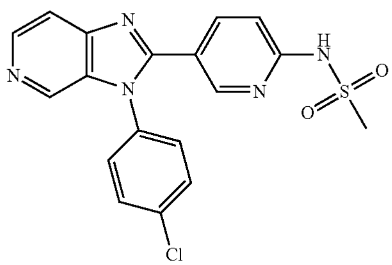 [SMILES: CS(=O)(=O)Nc1ccc(-c2nc3ccncc3n2-c2ccc(Cl)cc2)cn1] | N-{5-[3-(4-Chlorophenyl)-3H-imidazo[4,5-c]pyridin-2-yl]pyridin-2-yl}methanesulfonamide | From Intermediate 47<br>White solid<br>Yield 163 mg, 46.8%<br>LCMS (ES$^+$): 400.0 [MH]$^+$<br>HPLC: Rt 4.19 min, 100% purity |
| 17 | 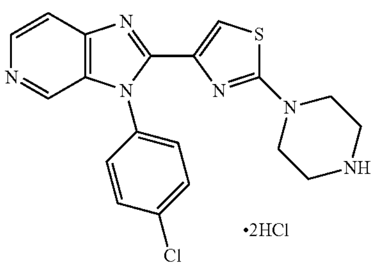 [SMILES: Clc1ccc(-n2c(-c3csc(N4CCNCC4)n3)nc3ccncc32)cc1] | 1-{4-[3-(4-Chlorophenyl)-3H-imidazo[4,5-c]pyridin-2-yl]-1,3-thiazol-2-yl}piperazine dihydrochloride | From Intermediate 48<br>Yellow solid<br>Yield 47.3 mg, 17.3% *<br>LCMS (ES$^+$): 397.0 [MH]$^+$<br>HPLC: Rt 3.44-3.55 min, 100% purity |
| 18 | 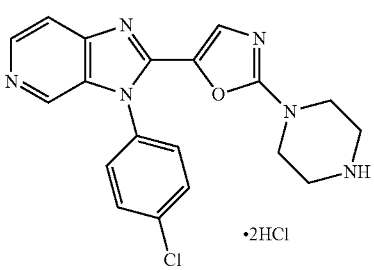 [SMILES: Clc1ccc(-n2c(-c3cnc(N4CCNCC4)o3)nc3ccncc32)cc1] | 1-{4-[3-(4-Chlorophenyl)-3H-imidazo[4,5-c]pyridin-2-yl]-1,3-oxazol-2-yl}piperazine dihydrochloride | From Intermediate 49<br>Orange solid<br>Yield 58.0 mg, 11.8% *<br>LCMS (ES$^+$): 381.1 [MH]$^+$<br>HPLC: Rt 3.26 min, 100% purity |
| 19 | 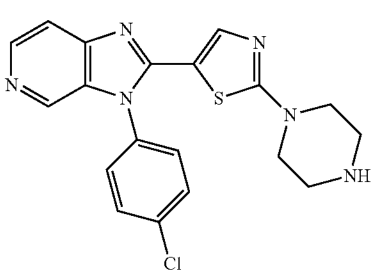 [SMILES: Clc1ccc(-n2c(-c3cnc(N4CCNCC4)s3)nc3ccncc32)cc1] | 1-{5-[3-(4-Chlorophenyl)-3H-imidazo[4,5-c]pyridin-2-yl]-1,3-thiazol-2-yl}piperazine | From Intermediate 50<br>Off white solid<br>Yield 9.50 mg, 3.0% *<br>LCMS (ES$^+$): 397.0 [MH]$^+$<br>HPLC; Rt 3.41, 3.53 min, 39.3% purity |

TABLE 4-continued

Cyclisation of Intermediates 33-45, 47-51 and 53

| Ex | Structure | Name | Intermediate(s), Form, Yield, LCMS, HPLC |
|---|---|---|---|
| 20 | 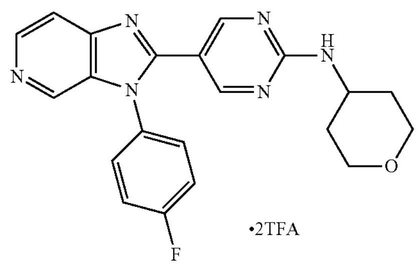 [SMILES: Fc1ccc(-n2c(-c3cnc(NC4CCOCC4)nc3)nc3ccncc32)cc1] | 5-[3-(4-Fluorophenyl)-3H-imidazo[4,5-c]pyridin-2-yl]-N-(oxan-4-yl)pyrimidin-2-amine | From Intermediate 51<br>White solid<br>Yield 79.0 mg, 13.9%<br>LCMS (ES⁺): 391.2 [MH⁺]<br>HPLC: Rt 4.47 min, 100% purity |

\* Boc deprotection under reaction conditions

Example 21

5-[3-(4-Chlorophenyl)-3H-imidazo[4,5-c]pyridin-2-yl]-1H-imidazol

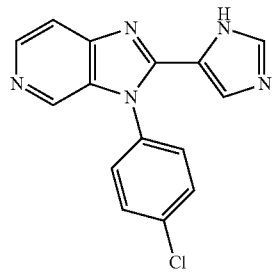 [SMILES: Clc1ccc(-n2c(-c3cnc[nH]3)nc3ccncc32)cc1]

Intermediate 1 (200 mg, 0.75 mmol) and imidazole-4-carboxaldehyde (86.8 mg, 0.90 mmol) were dissolved in EtOH (5 mL) and $Na_2S_2O_4$ (524 mg, 3.01 mmol) was added. The reaction mixture was heated using a microwave reactor at 160° C. for 1 h, diluted with sat aq $NaHCO_3$ (25 mL) and water (25 mL), and extracted into DCM (3×50 mL). The combined organic fractions were dried ($MgSO_4$) and concentrated in vacuo. The residue was purified by column chromatography to give the title compound as a yellow solid (51.2 mg, 23.0%). LCMS (ES⁺): 296.1 [MH]⁺. HPLC: Rt 3.24 min, 100% purity.

Examples 22-31

Examples 22-31 were prepared similarly to Example 21, by reductive condensation of Intermediates 1-3 with the appropriate aldehyde; see Table 5 below.

TABLE 5

Reductive condensations of Intermediates 1-3

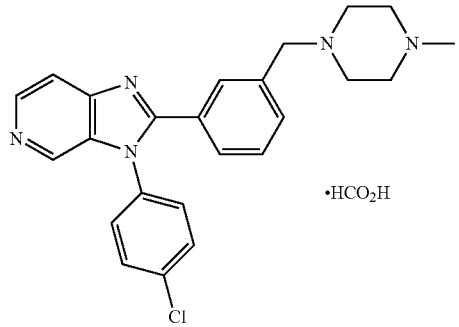 [SMILES: CN1CCN(Cc2cccc(-c3nc4ccncc4n3-c3ccc(Cl)cc3)c2)CC1 ; "·HCO2H"]

| Ex | Structure | Name | Intermediate(s) used, Form, Yield, LCMS, HPLC |
|---|---|---|---|
| 22 | 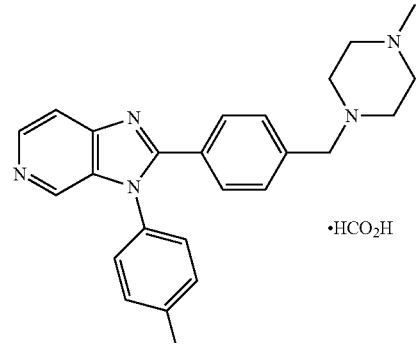 | 1-({3-[3-(4-Chlorophenyl)-3H-imidazo[4,5-c]pyridin-2-yl]phenyl}methyl)-4-methylpiperazine; formic acid | From Intermediate 1<br>White solid<br>Yield 34.6 mg, 9.9%<br>LCMS (ES+): 418.1 [MH]+<br>HPLC: Rt 3.51 min, 99.0% purity |
| 23 | 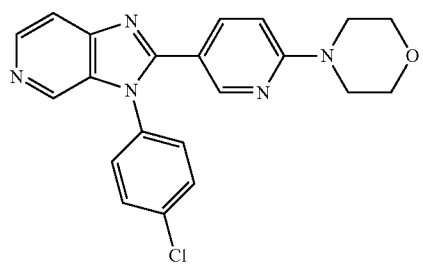 | 1-({4-[3-(4-Chlorophenyl)-3H-imidazo[4,5-c]pyridin-2-yl]phenyl}methyl)-4-methylpiperazine; formic acid | From Intermediate 1<br>Light yellow solid<br>Yield 42.0 mg, 12.0%<br>LCMS (ES+): 418.1 [MH]+ HPLC: Rt 3.43 min, 99.1% purity |
| 24 | 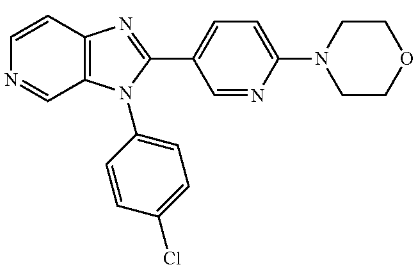 [SMILES: Clc1ccc(-n2c(-c3ccc(N4CCOCC4)nc3)nc3ccncc32)cc1] | 4-{5-[3-(4-Chlorophenyl)-3H-imidazo[4,5-c]pyridin-2-yl]pyridin-2-yl}morpholine | From Intermediate 1<br>White solid<br>Yield 70.9 mg, 20.8%<br>LCMS (ES+): 392.1 [MH]+<br>HPLC: Rt 4.49 min, 100% purity |
| 25 | 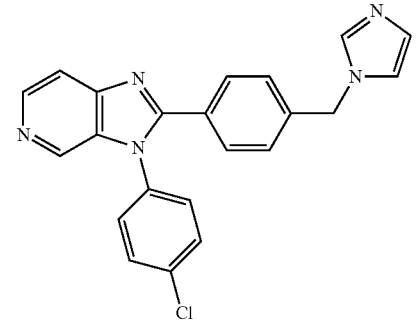 [SMILES: Clc1ccc(-n2c(-c3ccc(Cn4ccnc4)cc3)nc3ccncc32)cc1] | 1-({4-[3-(4-Chlorophenyl)-3H-imidazo[4,5-c]pyridin-2-yl]phenyl}methyl)-1H-imidazole | From Intermediate 1<br>Orange gum<br>Yield 39.4 mg, 11.4%<br>LCMS (ES+): 388.1 [MH]+<br>HPLC: Rt 3.90 min, 100% purity |

TABLE 5-continued

Reductive condensations of Intermediates 1-3

| Ex | Structure | Name | Intermediate(s) used, Form, Yield, LCMS, HPLC |
|---|---|---|---|
| 26 | 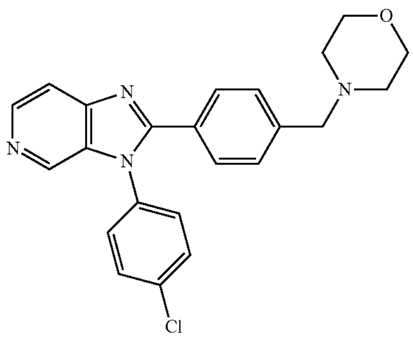 [SMILES: Clc1ccc(-n2c(-c3ccc(CN4CCOCC4)cc3)nc3ccncc32)cc1] | 4-({4-[3-(4-Chlorophenyl)-3H-imidazo[4,5-c]pyridin-2-yl]phenyl}methyl)morpholine | From Intermediate 1<br>Yellow solid<br>Yield 9.81 mg, 2.8%<br>LCMS (ES+): 405.1 [MH]+<br>HPLC: Rt 3.85 min, 100% purity |
| 27 | 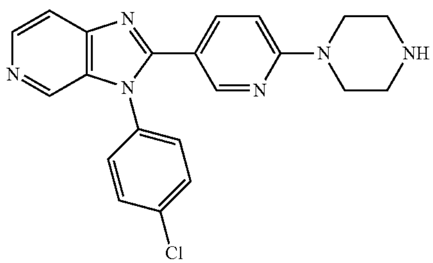 [SMILES: Clc1ccc(-n2c(-c3ccc(N4CCNCC4)nc3)nc3ccncc32)cc1] | 1-{5-[3-(4-Chlorophenyl)-3H-imidazo[4,5-c]pyridin-2-yl]pyridin-2-yl}piperazine | From Intermediate 1<br>Yellow solid<br>Yield 3.10 mg, 1.4% *<br>LCMS (ES+): 391.0 [MH]+<br>HPLC: Rt 3.51 min, 100% purity |
| 28 | 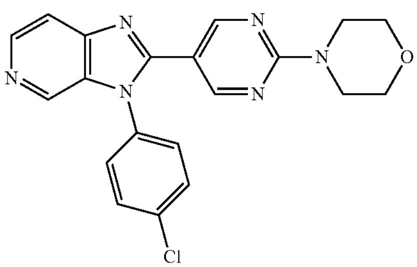 [SMILES: Clc1ccc(-n2c(-c3cnc(N4CCOCC4)nc3)nc3ccncc32)cc1] | 4-{5-[3-(4-Chlorophenyl)-3H-imidazo[4,5-c]pyridin-2-yl]pyrimidin-2-yl}morpholine | From Intermediate 1<br>White solid<br>2.75 mg, 0.7%<br>LCMS (ES+): 393.1 [MH]+<br>HPLC: Rt 5.08 min, 97.9% purity |
| 29 | 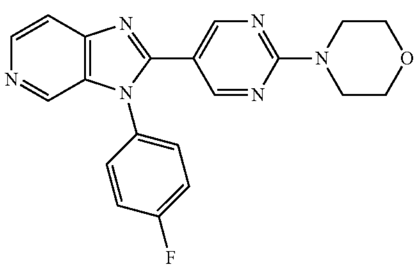 | 4-{5-[3-(4-Fluorophenyl)-3H-imidazo[4,5-c]pyridin-2-yl]pyrimidin-2-yl}morpholine | From Intermediate 2<br>White solid<br>Yield 168 mg, 36.8% LCMS (ES+): 377.1 [MH]+<br>HPLC: Rt 4.68 min, 98.1% purity |

TABLE 5-continued

Reductive condensations of Intermediates 1-3

| Ex | Structure | Name | Intermediate(s) used, Form, Yield, LCMS, HPLC |
|----|-----------|------|------------------------------------------------|
| 30 | 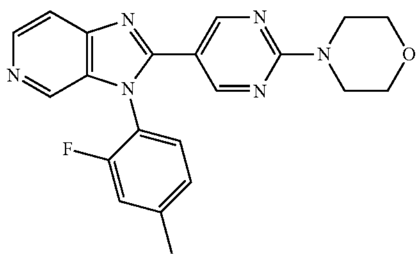 [SMILES: Cc1ccc(-n2c(-c3cnc(N4CCOCC4)nc3)nc3ccncc32)c(F)c1] | 4-{5-[3-(4-Fluoro-4-methylphenyl)-3H-imidazo[4,5-c]pyridin-2-yl]pyrimidin-2-yl}morpholine | From Intermediate 3<br>White solid<br>Yield 40.1 mg, 13.5%<br>LCMS<br>(ES+): 391.1 [MH]+ HPLC:<br>Rt 4.77 min, 99.3% purity |
| 31 | 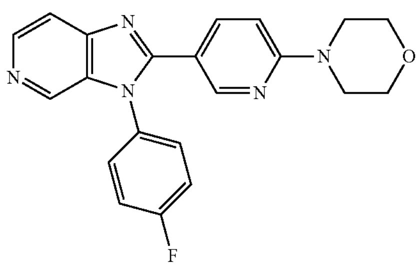 | 4-{5-[3-(4-Fluorophenyl)-3H-imidazo[4,5-c]pyridin-2-yl]pyridin-2-yl}morpholine | From Intermediate 2<br>White solid<br>Yield 42.1 mg, 14.0%<br>LCMS<br>(ES+): 376.1 [MH]+<br>HPLC: Rt 4.20 min, 98.2% purity |

\* Additional Boc deprotection step incorporated

Example 32

4-{5-[3-(4-Chloro-3-fluorophenyl)-3H-imidazo[4,5-c]pyridin-2-yl]pyrimidin-2-yl}morpholine

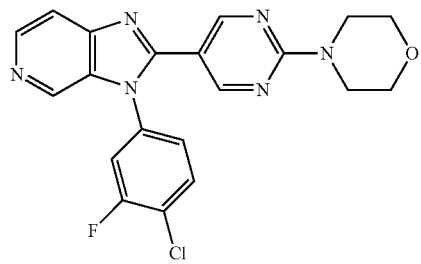 [SMILES: Fc1cc(-n2c(-c3cnc(N4CCOCC4)nc3)nc3ccncc32)ccc1Cl]

Intermediate 4 (200 mg, 0.75 mmol), 2-(morpholin-4-yl)pyrimidine-5-carbaldehyde (188 mg, 0.97 mmol) and Na$_2$S$_2$O$_4$ (250 mg, 2.99 mmol) were suspended in EtOH (5 mL) and the reaction mixture was heated using a microwave reactor at 160° C. for 1 h. The reaction mixture was diluted with 1M aq Na$_2$CO$_3$ (40 mL) and extracted into DCM (2×50 mL). The combined organic fractions were dried (MgSO$_4$) and concentrated in vacuo. The residue was purified by column chromatography and by reverse phase HPLC to give the title compound (36.6 mg, 11.9%) as an off-white solid. LCMS (ES+): 411.0 [MH]+. HPLC: Rt 5.09 min, 99.7% purity.

Example 33

4-{5-[3-(5-Chloropyridin-2-yl)-3H-imidazo[4,5-c]pyridin-2-yl]pyrimidin-2-yl}morpholine; tris(trifluoroacetic Acid)

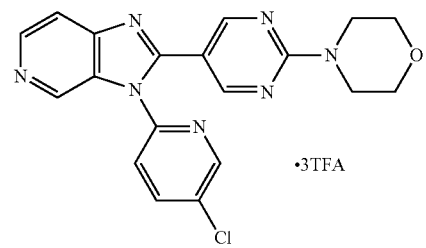 [SMILES: Clc1ccc(-n2c(-c3cnc(N4CCOCC4)nc3)nc3ccncc32)nc1]

Example 33 was prepared similarly to Example 32, using Intermediate 5 instead of Intermediate 4, to give the title compound (29.0 mg, 4.5%) as a white solid. LCMS (ES+): 394.0 [MH]+. HPLC: Rt 4.68 min, 97.8% purity.

Example 34

4-{5-[3-(5-Fluoropyridin-2-yl)-3H-imidazo[4,5-c]pyridin-2-yl]pyrimidin-2-yl}morpholine

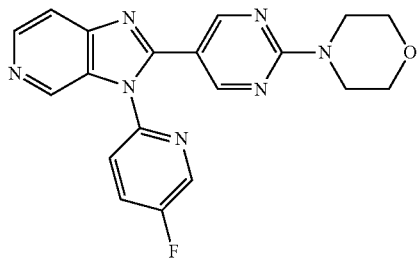 [SMILES: Fc1ccc(-n2c(-c3cnc(N4CCOCC4)nc3)nc3ccncc32)nc1]

Example 34 was prepared similarly to Example 32, using Intermediate 6 instead of Intermediate 4, to give the title compound (53.2 mg, 7.5%) as a white solid. LCMS (ES$^+$): 378.1 [MH]$^+$. HPLC: Rt 4.36 min, 98.4% purity.

Example 35

4-{5-[3-(4-Chlorophenyl)-3H-imidazo[4,5-c]pyridin-2-yl]pyridin-2-yl}piperazine-1-carboxamide Dihydrochloride

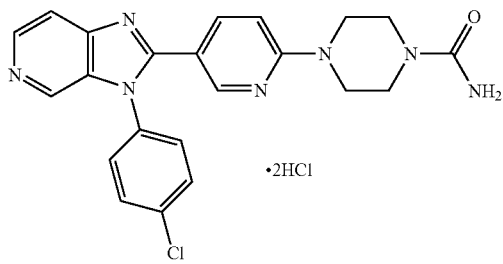 [SMILES: NC(=O)N1CCN(c2ccc(-c3nc4ccncc4n3-c3ccc(Cl)cc3)cn2)CC1]

Example 27 trihydrochloride (94.5 mg, 0.19 mmol) was dissolved in DCM (5 mL), and DIPEA (145 uL, 0.83 mmol) and trimethylsilyl isocyanate (30.7 uL, 0.23 mmol) were added. The reaction mixture was stirred for 16 h, diluted with 1M aq Na$_2$CO$_3$ (25 mL) and extracted into DCM (3×25 mL). The combined organic fractions were dried (MgSO$_4$) and concentrated in vacuo. The residue was dissolved in 1.25M HCl in EtOH (5 mL), stirred for 1 h and concentrated in vacuo. The residue was purified by reverse phase HPLC to give the title compound (21.4 mg, 22.3%) as a yellow solid. LCMS (ES$^+$): 434.1 [MH]$^+$. HPLC: Rt 4.19 min, 98.5% purity.

Example 36

N-(1-{5-[3-(4-Chlorophenyl)-3H-imidazo[4,5-c]pyridin-2-yl]pyridin-2-yl}piperidin-4-yl)acetamide

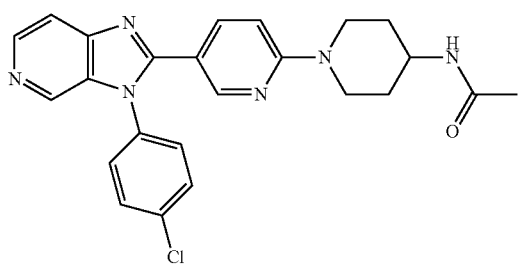 [SMILES: CC(=O)NC1CCN(c2ccc(-c3nc4ccncc4n3-c3ccc(Cl)cc3)cn2)CC1]

Example 8 (100 mg, 0.25 mmol), Et$_3$N (41.2 uL, 0.30 mmol) and acetyl chloride (19.3 uL, 0.27 mmol) were dissolved in DCM (15 mL) and the reaction mixture was stirred for 2 h and concentrated in vacuo. The residue was purified by column chromatography and partitioned between DCM (20 mL) and sat aq NaHCO$_3$ (20 mL). The organic fraction was washed with sat aq NaHCO$_3$ (20 mL), dried (MgSO$_4$) and concentrated in vacuo to give the title compound (61.6 mg, 55.8%) as a light yellow solid. LCMS (ES$^+$): 447.0 [MH]$^+$. HPLC: Rt 3.98 min, 99.7% purity.

Example 37

1-(4-{5-[3-(4-Fluorophenyl)-3H-imidazo[4,5-c]pyridin-2-yl]pyridin-2-yl}piperazin-1-yl)ethan-1-one

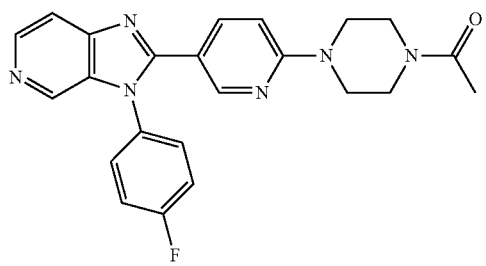 [SMILES: CC(=O)N1CCN(c2ccc(-c3nc4ccncc4n3-c3ccc(F)cc3)cn2)CC1]

Example 37 was prepared similarly to Example 36, using Intermediate 52 instead of Example 8, to give the title compound (227 mg, 38.7%) as a white solid. LCMS (ES$^+$): 417.1 [MH]$^+$. HPLC: Rt 4.26 min, 100% purity.

Example 38

1-(4-{5-[3-(4-fluorophenyl)-3H-imidazo[4,5-c]pyridin-2-yl]pyridin-2-yl}-1,4-diazepan-1-yl)ethan-1-one; bis(trifluoroacetic Acid)

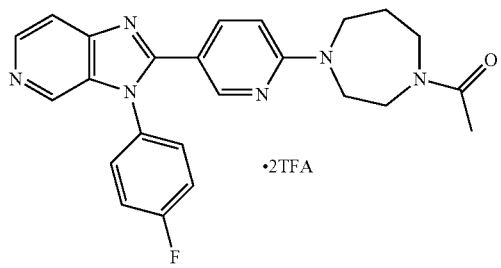 [SMILES: CC(=O)N1CCCN(c2ccc(-c3nc4ccncc4n3-c3ccc(F)cc3)cn2)CC1]

Example 38 was prepared similarly to Example 36, using Intermediate 55 instead of Example 8, to give the title compound (143 mg, 41.2%) as a pink gum. LCMS (ES$^+$): 431.1 [MH]$^+$. HPLC: Rt 4.41 min, 99.7% purity.

Example 39

N-(1-{5-[3-(4-Chlorophenyl)-3H-imidazo[4,5-c]pyridin-2-yl]pyridin-2-yl}piperidin-4-yl)methanesulfonamide

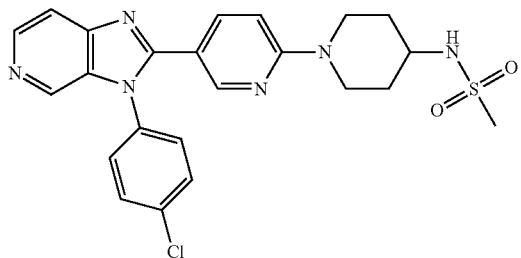 [SMILES: CS(=O)(=O)NC1CCN(c2ccc(-c3nc4ccncc4n3-c3ccc(Cl)cc3)cn2)CC1]

Example 8 (100 mg, 0.25 mmol), Et₃N (41.2 uL, 0.30 mmol) and methanesulfonyl chloride (26.8 uL, 0.35 mmol) were dissolved in DCM (15 mL) and the reaction mixture was stirred for 2 h, diluted with DCM (20 mL), washed with sat aq NaHCO₃ (30 mL), dried (MgSO₄) and concentrated in vacuo. The residue was triturated from MeOH (3 mL) and collected by filtration to give the title compound (30.6 mg, 25.7%) as a yellow solid. LCMS (ES⁺): 483.0 [MH]⁺. HPLC: Rt 4.18 min, 97.3% purity.

Example 40

1-{5-[3-(4-Fluorophenyl)-3H-imidazo[4,5-c]pyridin-2-yl]pyridin-2-yl}-4-methanesulfonylpiperazin

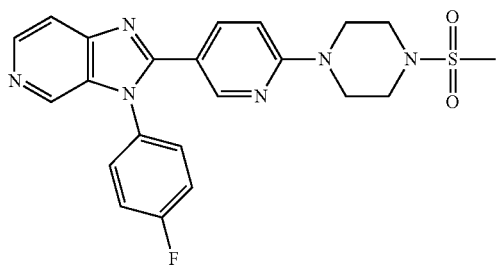 [SMILES: CS(=O)(=O)N1CCN(c2ccc(-c3nc4ccncc4n3-c3ccc(F)cc3)cn2)CC1]

Example 40 was prepared similarly to Example 39, using Intermediate 52 instead of Example 8, to give the title compound (44.5 mg, 10.3%) as a yellow solid. LCMS (ES⁺): 453.0 [MH]⁺. HPLC: Rt 4.59 min, 98.2% purity.

Example 41

(1-{5-[3-(4-Chlorophenyl)-3H-imidazo[4,5-c]pyridin-2-yl]pyridin-2-yl}piperidin-4-yl)urea; bis(trifluoroacetic Acid)

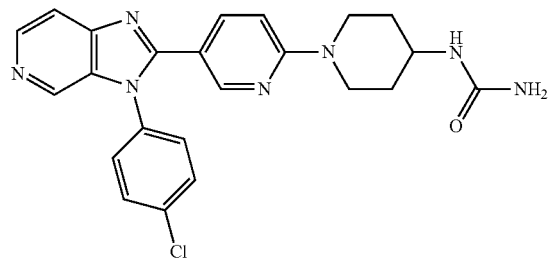 [SMILES: NC(=O)NC1CCN(c2ccc(-c3nc4ccncc4n3-c3ccc(Cl)cc3)cn2)CC1]

Example 8 (100 mg, 0.25 mmol), Et₃N (41.2 uL, 0.30 mmol) and trimethylsilyl isocyanate (36.4 uL, 0.27 mmol) were dissolved in DCM (15 mL) and the reaction mixture was stirred for 24 h. Further trimethylsilyl isocyanate (16.6 uL, 0.12 mmol) was added and the reaction mixture was stirred for 24 h. The reaction mixture was diluted with DCM (50 mL), washed with water (30 mL), sat aq NaHCO₃ (30 mL), dried (MgSO₄) and concentrated in vacuo. The residue was purified by reverse phase HPLC to give the title compound (36.3 mg, 21.7%) as a yellow solid. LCMS (ES⁺): 448.1 [MH]⁺. HPLC: Rt 3.75 min, 98.7% purity.

Example 42

4-{5-[3-(4-Fluorophenyl)-3H-imidazo[4,5-c]pyridin-2-yl]pyridin-2-yl}piperazine-1-carboxamide

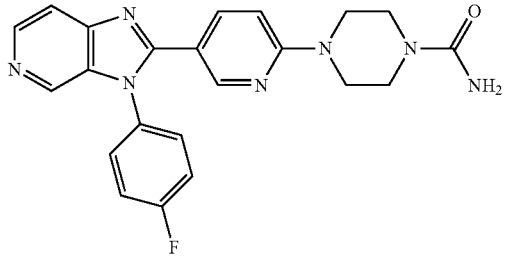 [SMILES: NC(=O)N1CCN(c2ccc(-c3nc4ccncc4n3-c3ccc(F)cc3)cn2)CC1]

Example 42 was prepared similarly to Example 41, using Intermediate 52 instead of Example 8, to give the title compound (44.0 mg, 11.1%) as a white solid. LCMS (ES⁺): 418.0 [MH]⁺. HPLC: Rt 3.88 min, 100% purity.

Example 43

4-{5-[3-(4-Chlorophenyl)-3H-imidazo[4,5-c]pyridin-2-yl]-1,3-oxazol-2-yl}piperazine-1-carboxamide

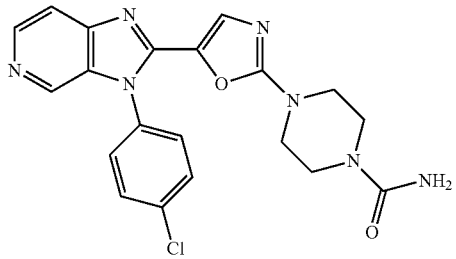 [SMILES: NC(=O)N1CCN(c2ncc(-c3nc4ccncc4n3-c3ccc(Cl)cc3)o2)CC1]

Example 43 was prepared similarly to Example 41, using Example 18 instead of Example 8, to give the title compound (7.20 mg, 7.7%) as a pale yellow solid. LCMS (ES⁺): 424.0 [MH]⁺. HPLC: Rt 4.20 min, 99.7% purity.

Example 44

4-{5-[3-(4-Fluorophenyl)-3H-imidazo[4,5-c]pyridin-2-yl]pyridin-2-yl}-1,4-diazepane-1-carboxamide

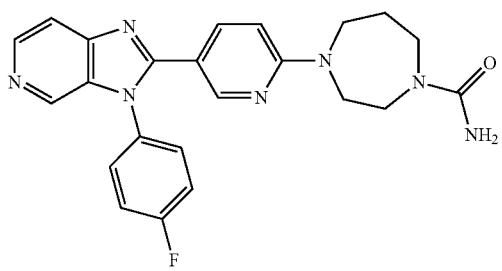 [SMILES: NC(=O)N1CCCN(c2ccc(-c3nc4ccncc4n3-c3ccc(F)cc3)cn2)CC1]

Example 44 was prepared similarly to Example 41, using Intermediate 55 instead of Example 8, to give the title compound (56.7 mg, 24.9%) as a pink solid. LCMS (ES+): 432.1 [MH]+. HPLC: Rt 3.83 min, 99.0% purity.

Example 45

4-(5-{3-Phenyl-3H-imidazo[4,5-c]pyridin-2-yl}pyrimidin-2-yl)morpholine

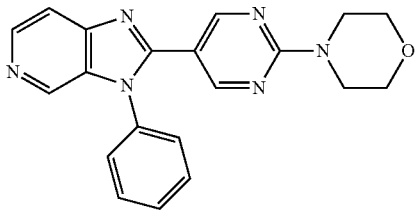 [SMILES: c1ccc(-n2c(-c3cnc(N4CCOCC4)nc3)nc3ccncc32)cc1]

Example 28 (115 mg, 0.29 mmol) was suspended in EtOH (5 mL) and ammonium formate (148 mg, 2.34 mmol) and 10% Pd/C (50.0 mg) were added. The reaction mixture was heated under reflux for 5 h, filtered through Celite and concentrated in vacuo. The residue was dissolved in DCM (50 mL), washed with 1M aq Na$_2$CO$_3$ (50 mL) dried (MgSO$_4$) and concentrated in vacuo. The residue was purified by column chromatography to give the title compound (40.2 mg, 38.9%) as a white solid. LCMS (ES+): 359.1 [MH]+. HPLC: Rt 4.65 min, 99.8% purity.

Example 46

4-[1-(4-Chlorophenyl)-1H-pyrrolo[2,3-c]pyridin-2-yl]pyridine

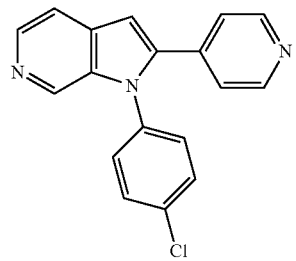 [SMILES: Clc1ccc(-n2c(-c3ccncc3)cc3ccncc32)cc1]

Intermediate 56 (100 mg, 0.44 mmol) and triisopropyl borate (212 uL, 0.92 mmol) were dissolved in THF (5 mL) and the reaction mixture was cooled to 0° C. LDA (435 uL, 2.0M in THF/heptane, 0.87 mmol) was added and the reaction mixture was stirred at 0° C. for 30 min. The reaction was quenched with water (2 mL) and diluted with dioxane (3 mL). 4-iodopyridine (108 mg, 0.52 mmol), Pd(PPh$_3$)$_4$ (40.4 mg, 0.03 mmol) and a solution of Na$_2$CO$_3$ (139 mg, 1.31 mmol) in water (4 mL) were added. The reaction mixture was heated using a microwave reactor at 160° C. for 20 min. The reaction mixture was partitioned between water (40 mL) and EtOAc (40 mL), and the organic fraction was dried (MgSO$_4$) and concentrated in vacuo. The residue was purified by reverse phase HPLC to give the title compound as a light yellow solid (21.8 mg, 16.3%). LCMS (ES+): 306.1 [MH]+. HPLC: Rt 3.52 min, 99.9% purity.

Examples 47-53

Examples 47-53 were prepared similarly to Example 46, by borate formation and Suzuki reaction of Intermediate 56 with the appropriate aryl or heteroaryl iodide or bromide; see Table 6 below.

TABLE 6

Borate formation and Suzuki reactions of Intermediate 56

| Ex | Structure | Name | Intermediate(s) Form, Yield, LCMS, HPLC |
|---|---|---|---|
| 47 | 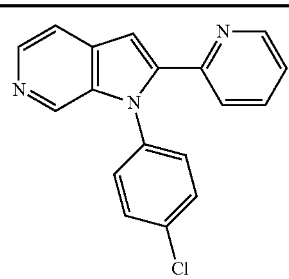 | 2-[1-(4-Chlorophenyl)-1H-pyrrolo[2,3-c]pyridin-2-yl]pyridine | Yellow gum Yield 14.0 mg, 7.0% LCMS (ES+): 306.1 [MH]+ HPLC: Rt 4.82 min, 99.1% purity |

TABLE 6-continued

Borate formation and Suzuki reactions of Intermediate 56

| Ex | Structure | Name | Intermediate(s) Form, Yield, LCMS, HPLC |
|---|---|---|---|
| 48 | 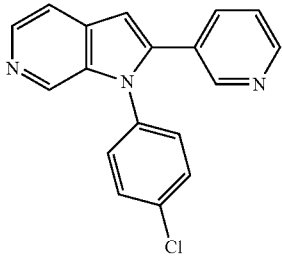 [SMILES: Clc1ccc(-n2c(-c3cccnc3)cc3ccncc32)cc1] | 3-[1-(4-Chlorophenyl)-1H-pyrrolo[2,3-c]pyridin-2-yl]pyridine | Yellow gum<br>Yield 13.1 mg, 9.80%<br>LCMS<br>(ES$^+$): 306.1 [MH]$^+$ HPLC: Rt 3.95 min, 99.1% purity |
| 49 | 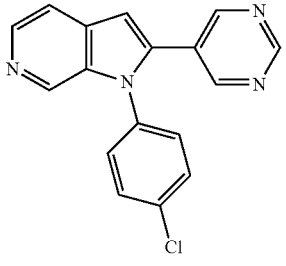 [SMILES: Clc1ccc(-n2c(-c3cncnc3)cc3ccncc32)cc1] | 5-[1-(4-Chlorophenyl)-1H-pyrrolo[2,3-c]pyridin-2-yl]pyrimidine | White solid<br>Yield 84.9 mg; 32.2%<br>LCMS (ES$^+$): 307.0 [MH]$^+$<br>HPLC: Rt 4.24 min, 99.1% purity |
| 50 | 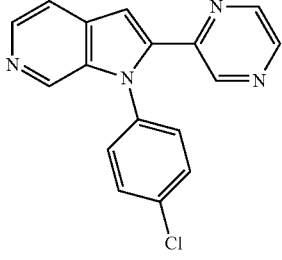 | 2-[1-(4-Chlorophenyl)-1H-pyrrolo[2,3-c]pyridin-2-yl]pyrazine | Yellow gum<br>Yield 28.0 mg, 13.9%<br>LCMS (ES$^+$): 307.0 [MH]$^+$<br>HPLC: Rt 4.53 min, 99.7% purity |
| 51 | 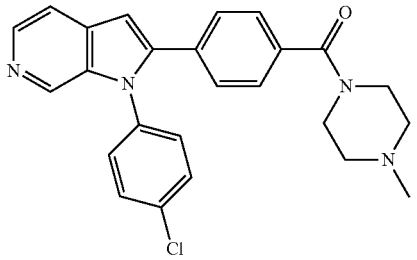 [SMILES: CN1CCN(C(=O)c2ccc(-c3cc4ccncc4n3-c3ccc(Cl)cc3)cc2)CC1] | 1-({4-[1-(4-Chlorophenyl)-1H-pyrrolo[2,3-c]pyridin-2-yl]phenyl}carbonyl)-4-methylpiperazine | Using Intermediate 57<br>Yellow solid<br>Yield 23.0 mg, 8.1%<br>LCMS (ES$^+$): 431.1 [MH]$^+$<br>HPLC: Rt 3.77 min, 97.9% purity |

TABLE 6-continued

Borate formation and Suzuki reactions of Intermediate 56

| Ex | Structure | Name | Intermediate(s) Form, Yield, LCMS, HPLC |
|---|---|---|---|
| 52 | 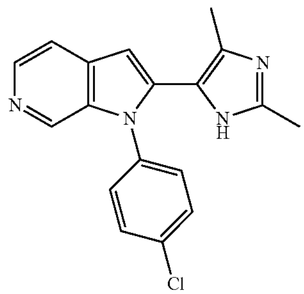 [SMILES: Cc1nc(C)c(-c2cc3ccncc3n2-c2ccc(Cl)cc2)[nH]1] | 5-[1-(4-Chlorophenyl)-1H-pyrrolo[2,3-c]pyridin-2-yl]-2,4-dimethyl-1H-imidazole | Off white solid<br>Yield 14.6 mg, 6.9%<br>LCMS (ES$^+$): 323.1 [MH]$^+$<br>HPLC: Rt 3.45 min, 100% purity |
| 53 | 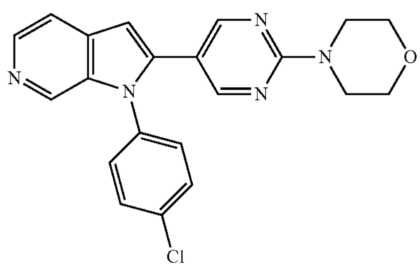 [SMILES: Clc1ccc(-n2c(-c3cnc(N4CCOCC4)nc3)cc3ccncc32)cc1] | 4-{5-[1-(4-Chlorophenyl)-1H-pyrrolo[2,3-c]pyridin-2-yl]pyrimidin-2-yl}morpholine | Yellow solid<br>Yield 67.2 mg, 19.6%<br>LCMS (ES$^+$): 392.1 [MH]$^+$<br>HPLC: Rt 5.12 min, 100% purity |

Biological Tests
Biological Assays of the SSAO Enzyme Inhibitors

All primary assays were performed at RT. with purified recombinantly expressed human SSAO. Enzyme was prepared essentially as described in Öhman et al. (Protein Expression and Purification 46 (2006) 321-331). In addition, secondary- and selectivity assays were performed using SSAO prepared from various tissues or purified rat recombinant SSAO. The enzyme activity was assayed with benzylamine as substrate by measuring either benzaldehyde production, using $^{14}$C-labeled substrate, or by utilizing the production of hydrogen peroxide in a horseradish peroxidase (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and compounds in 50 mM sodium phosphate, pH 7.4 were set to pre-incubate in flat-bottomed microtiter plates for approximately 15 min before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 h, exciting at 544 nm and reading the emission at 590 nm. For the human SSAO assay final concentrations of the reagents in the assay wells were: SSAO enzyme 1 ug/ml, benzylamine 100 uM, Amplex reagent 20 uM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

Aldehyde Detection:

SSAO activity was assayed using 14C-labeled benzylamine and analysed by measuring radioactive benzaldehyde. In a white 96-well optiplate (Packard), 20 uL of diluted test compound was pre-incubated at room temperature with 20 uL SSAO enzyme for approximately 15 min with continuous agitation. All dilutions were made with PBS. The reaction was initiated by adding 20 uL of the benzylamine substrate solution containing [7-14C] Benzylamine hydrochloride (CFA589, GE Healthcare). The plate was incubated for 1 h as above after which the reaction was stopped by acidification (10 uL 1M aq HCl). Then 90 uL Micro Scint-E solution (Perkin-Elmer) was added to each well and the plate was continuously mixed for 15 min. Phase separation occurred instantly and activity was read in a Topcount scintillation counter (Perkin-Elmer). In the final reaction well, the human recombinant SSAO concentration was 10 ug/ml. In order to optimize sensitivity, the substrate concentration was decreased as compared to the HRP coupled assay in order to get a higher fraction of radioactive product. In the human SSAO assay, benzylamine concentration was 40 uM (0.2 uCi/mL). Data was analysed as above.

All of the exemplified compounds of the invention had an $IC_{50}$ value of between 5 nM and 900 nM at SSAO.

The invention claimed is:

1. A compound of formula (I) or a pharmaceutically acceptable salt, or N-oxide thereof:

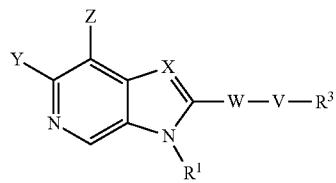

(I)

wherein:
Y is selected from hydrogen, hydroxyl, —$NH_2$, —NH—$C_{1-4}$-alkyl, —NH-halo-$C_{1-4}$-alkyl, or —$C_{1-4}$-alkoxy;
Z is selected from hydrogen, halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, or —NHhalo-$C_{1-4}$-alkyl;
$R^1$ is a phenyl ring, or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, and —$NR^6S(O)_2R^5$; wherein
$R^{4A}$, $R^{4B}$ $R^5$ and $R^6$ are each independently selected from hydrogen, $C_{1-4}$-alkyl or halo-$C_{1-4}$-alkyl, or
$R^{4A}$ and $R^{4B}$ together with the nitrogen to which they are attached form a 3-7 membered cyclic amino group, optionally substituted by one or more substituents selected from: halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, —NHhalo-$C_{1-4}$-alkyl;
X is —N═;
W is a phenyl ring or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^{7A}R^{7B}$, —$NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$;
$R^{7A}$ and $R^{7B}$ are independently hydrogen, $C_{1-4}$-alkyl or halo-$C_{1-4}$-alkyl,
V is selected from a bond, —O—, —$N(R^6)$—, —(C═O)—, —$CONR^6$—, —$NR^6C(O)$—, or —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —$N(R^6)$—;
$R^3$ is hydrogen or a 3-7 membered heterocyclic ring, or a cycloalkyl ring selected from cyclopropyl, cyclopentyl and cyclohexyl, or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR^5$, $NR^{4A}R^{4B}$, $NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$.

2. The compound according to claim 1 wherein Y is hydrogen.

3. The compound according to claim 1 wherein Z is hydrogen.

4. The compound according to claim 1 wherein $R^1$ is phenyl or 6-membered heteroaryl, optionally substituted with one or more substituents selected from halogen, $C_{1-4}$-alkyl or halo-$C_{1-4}$-alkyl.

5. The compound according to claim 1 wherein $R^1$ is phenyl or pyridyl, optionally substituted with one or more substituents selected from F, Cl or $CH_3$.

6. The compound according to claim 1 wherein W is a phenyl ring optionally substituted with one or more substituents selected from halogen, cyano, $C_{1-4}$-alkyl, halo-$C_{1-4}$-alkyl, cyano-$C_{1-4}$-alkyl, —$OR_5$, —$NR^{7A}R^{7B}$, $NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$.

7. The compound according to claim 1 wherein W is a 6-membered heterocyclic ring selected from pyridine, pyridazine, pyrazine, or pyrimidine optionally substituted with one or more substituents selected from halogen, cyano, $C_{1-4}$-alkyl, halo-$C_{1-4}$-alkyl, cyano-$C_{1-4}$-alkyl, —$OR_5$, —$NR^{7A}R^{7B}$, $NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$.

8. The compound according to claim 1 wherein W is a 5-membered ring selected from oxazole, thiazole or imidazole optionally substituted with one or more substituents selected from halogen, cyano, $C_{1-4}$-alkyl, halo-$C_{1-4}$-alkyl, cyano-$C_{1-4}$-alkyl, —$OR_5$, —$NR^{7A}R^{7B}$, $NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$.

9. The compound according to claim 1 wherein W is substituted with one or more substituents selected from fluoro, chloro, cyano, $CH_3$ or $CF_3$.

10. The compound according to claim 1 wherein V is —$CH_2$—, —$(CH_2)_2$—, or —$N(R^6)CH_2$—, or —$CH_2$—N$(R^6)$—.

11. The compound according to claim 1 wherein $R^3$ is cyclopropyl, cyclopentyl or cyclohexyl optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR_5$, —$NR^{4A}R^{4B}$, $NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$.

12. The compound according to claim 1 wherein $R^3$ is formed from —$NR^{4A}R^{4B}$ wherein $R^{4A}$ and $R^{4B}$, together with the nitrogen atom to which they are attached join together to form a 4-7 membered heterocyclic ring optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR^5$, —$NR^{4A}R^{4B}$, $NR^6C(O)OR^5$, —$NR^6C(O)R^5$, —$NR^6C(O)NR^{4A}R^{4B}$, —$C(O)NR^{4A}R^{4B}$, —$C(O)R^5$, —C$(O)OR^5$, —$SO_2R^5$, —$SO_2NR^{4A}R^{4B}$ and —$NR^6S(O)_2R^5$.

13. The compound according to claim 1 wherein R³ is selected from

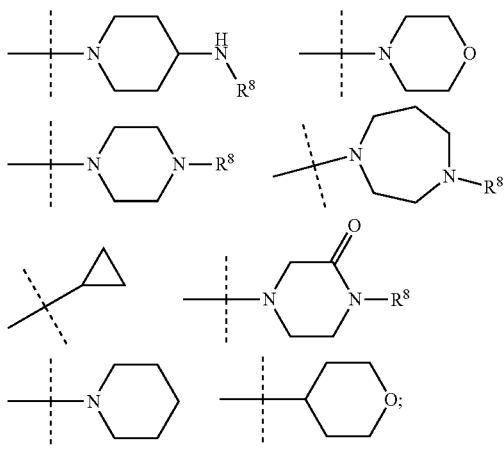

wherein R⁸ is selected from hydrogen, CH₃, —CONH₂, —NHCONH₂, —S(O)₂CH₃, and —COCH₃.

14. The compound according to claim 1 wherein X is —N═, and V is a direct bond.

15. The compound according to claim 1 selected from:
4-({5-[3-(4-Chlorophenyl)-3H-imidazo[4,5-c]pyridin-2-yl]pyridin-2-yl}methyl)morpholine;
4-{5-[3-(4-Fluorophenyl)-3H-imidazo[4,5-c]pyridin-2-yl]pyrimidin-2-yl}piperazin-2-one;
4-{5-[3-(4-Chlorophenyl)-3H-imidazo[4,5-c]pyridin-2-yl]pyrimidin-2-yl}piperazin-2-one;
5-[3-(4-Fluorophenyl)-3H-imidazo[4,5-c]pyridin-2-yl]-N-(oxan-4-yl)pyrimidin-2-amine;
4-{5-[3-(4-Fluorophenyl)-3H-imidazo[4,5-c]pyridin-2-yl]pyrimidin-2-yl}morpholine;
4-{5-[3-(2-Fluoro-4-methylphenyl)-3H-imidazo[4,5-c]pyridin-2-yl] pyrimidin-2-yl}morpholine;
N-(1-{5-[3-(4-Chlorophenyl)-3H-imidazo[4,5-c]pyridin-2-yl]pyridin-2-yl}piperidin-4-yl)acetamide;
1-(4-{5-[3-(4-Fluorophenyl)-3H-imidazo[4,5-c]pyridin-2-yl]pyridin-2-yl}piperazin-1-yl)ethan-1-one;
1-{5-[3-(4-Fluorophenyl)-3H-imidazo[4,5-c]pyridin-2-yl]pyridin-2-yl}-4-methanesulfonylpiperazine;
(1-{5-[3-(4-Chlorophenyl)-3H-imidazo[4,5-c]pyridin-2-yl]pyridin-2-yl}piperidin-4-yl)urea;
4-{5-[3-(4-Fluorophenyl)-3H-imidazo[4,5-c]pyridin-2-yl]pyridin-2-yl}piperazine-1-carboxamide;
and pharmaceutically acceptable salts thereof.

16. A pharmaceutical composition comprising a compound according to claim 1 together with one or more pharmaceutically acceptable carriers and/or excipients.

* * * * *